US008334235B2

(12) United States Patent
Cristau et al.

(10) Patent No.: US 8,334,235 B2
(45) Date of Patent: Dec. 18, 2012

(54) THIADIAZOLYLOXYPHENYLAMIDINES AND USE THEREOF AS FUNGICIDES

(75) Inventors: Pierre Cristau, Lyons (FR); Jörg Nico Greul, Leichlingen (DE); Ulrich Heinemann, Leichlingen (DE); Klaus Kunz, Düsseldorf (DE); Oswald Ort, Leverkusen (DE); Thomas Seitz, Langenfeld (DE); Arnd Voerste, Köln (DE); Peter Dahmen, Neuss (DE); Ulrike Wachendorff-Neumann, Neuwied (DE); Klaus-Günther Tietjen, Langenfeld (DE); Hiroyuki Hadano, Tochigi (JP)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/000,268

(22) PCT Filed: Jun. 19, 2009

(86) PCT No.: PCT/EP2009/004307
§ 371 (c)(1),
(2), (4) Date: Mar. 9, 2011

(87) PCT Pub. No.: WO2009/156074
PCT Pub. Date: Dec. 30, 2009

(65) Prior Publication Data
US 2011/0152080 A1 Jun. 23, 2011

(30) Foreign Application Priority Data
Jun. 27, 2008 (EP) .................................... 08159267

(51) Int. Cl.
*A01C 1/06* (2006.01)
*A01P 1/00* (2006.01)
*A01P 3/00* (2006.01)
*C07D 417/12* (2006.01)

(52) U.S. Cl. ........ 504/100; 514/326; 514/361; 546/209; 548/128; 548/129

(58) Field of Classification Search .................. 504/100; 514/326, 361; 546/209; 548/128, 129
See application file for complete search history.

(56) References Cited

U.S. PATENT DOCUMENTS

| | | | |
|---|---|---|---|
| 3,917,630 | A | 11/1975 | Hambock et al. |
| 4,245,432 | A | 1/1981 | Dannelly |
| 4,272,417 | A | 6/1981 | Barke et al. |
| 4,808,430 | A | 2/1989 | Kouno |
| 5,405,853 | A | 4/1995 | Baker et al. |
| 5,876,739 | A | 3/1999 | Turnblad et al. |
| 6,893,650 | B1 * | 5/2005 | Charles et al. ................. 424/405 |
| 2003/0176428 | A1 | 9/2003 | Schneidersmann et al. |
| 2004/0241098 | A1 | 12/2004 | Labourdette et al. |
| 2010/0105553 | A1 * | 4/2010 | Kunz et al. .................... 504/100 |

FOREIGN PATENT DOCUMENTS

| | | |
|---|---|---|
| DE | 960 281 | 3/1957 |
| DE | 22 42 185 | 3/1973 |
| WO | 89/10396 | 11/1989 |
| WO | 96/33270 | 10/1996 |
| WO | 00/46184 | 8/2000 |
| WO | 02/28186 | 4/2002 |
| WO | 02/080675 | 10/2002 |
| WO | 03/024219 | 3/2003 |
| WO | 03/093224 | 11/2003 |
| WO | 2004/037239 | 5/2004 |
| WO | 2004/041777 | 5/2004 |
| WO | 2005/007636 | 1/2005 |
| WO | 2007/024782 | 3/2007 |
| WO | 2007/027777 | 3/2007 |
| WO | 2007/031513 | 3/2007 |
| WO | 2008/110278 | 9/2008 |

OTHER PUBLICATIONS

International Search Report Based on PCT/EP2009/004307 Dated Jan. 21, 2010.
Goerdeler et al.; "Synthese Von 5-Chlor-1.2.4-Thiodiazolen Aus Perchlormethylmercaptan Und Amidinen"; Aus Dem Chemischen Institut Der Universitaet Bonn; 90; 1957; pp. 182-187.
Houben-Weyl; "Synthese Von Carbonsaeureamiden Aus Aminen Und Carbonsaeurederivaten"; 4th Edition; 2000; pp. 655-665. Galt et al.; "The Interaction of Amides With Amines: A General Method of Acylation"; 1943; pp. 1567-1567; vol. 65.
Hodgson et al.; "Nitrosation of 4-Halogeno-O- and M-Cresols and Oximation of the 4-Halogeno-2: 5-Toluquinones"; Journal of the Chemical Society; 1926; pp. 2036-2040.
Kohara et al.; A Facile Synthesis of 3-Substituted 5-Oxo-1,2,4-Thiadiazoles From Amidoximes [1]; J. Heterocyclic Chem. 37, Nov.-Dec. 2000; pp. 1419-1423.
Woerffel et al.; "5-Sulfanilamido- Und 3-Sulfanilamido-1,2,4-Thiodiazole"; vol. 295; 1962; pp. 811-816.
Goerdeler et al.; "Darstellung Und Eigenschaften Des 1.2.4- Und Des 1.3.4-Thiodiazols" Chem. Ber.; vol. 89; 1956, pp. 1534-1543.

* cited by examiner

Primary Examiner — Yong Chu
(74) Attorney, Agent, or Firm — Baker Donelson Bearman, Caldwell & Berkowitz, PC

(57) ABSTRACT

The present invention relates to thiadiazolyloxyphenylamidines of the general formula (I), to a process for the preparation thereof, to the use of the amidines according to the invention in combating undesirable microorganisms and to a composition for this purpose comprising the thiadiazolyloxyphenylamidines according to the invention. The invention furthermore relates to a method for combating undesirable microorganisms by application of the compounds according to the invention to the microorganisms and/or to the habitat thereof.

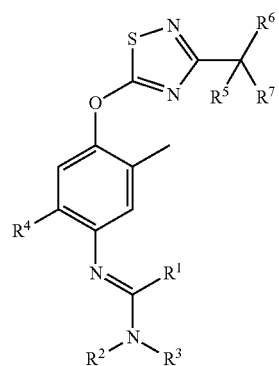

14 Claims, No Drawings

THIADIAZOLYLOXYPHENYLAMIDINES AND USE THEREOF AS FUNGICIDES

CROSS REFERENCE TO RELATED APPLICATIONS

This application is a §371 National Stage Application of PCT/EP2009/004307 filed Jun. 16, 2009 which claims priority to EP Application No. 08159267.7 filed Jun. 27, 2008, the entire contents of which is hereby incorporated by reference in their entirety.

BACKGROUND OF THE INVENTION

1. Field of the Invention

The present invention relates to thiadiazolyloxyphenylamidines of the general formula (I), to a process for the preparation thereof, to the use of the amidines according to the invention in combating undesirable microorganisms and to a composition for this purpose comprising the thiadiazolyloxyphenylamidines according to the invention. The invention furthermore relates to a method for combating undesirable microorganisms by application of the compounds according to the invention to the microorganisms and/or to the habitat thereof.

2. Description of Related Art

WO-A-00/046 184 discloses the use of amidines as fungicides.

WO-A-03/093 224 discloses the use of arylamidine derivatives as fungicides.

WO-A-03/024 219 discloses fungicidal compositions comprising at least one N2-phenylamidine derivative in combination with an additional selected known active substance.

WO-A-04/037 239 discloses fungicidal medicaments based on N2-phenylamidine derivatives.

WO-A-07/031 513 discloses thiadiazolyl-substituted phenylamidines and the preparation and use thereof as fungicides.

The effectiveness of the amidines described in the state of the art is good but in many cases leaves something to be desired.

SUMMARY OF THE INVENTION

It is therefore an object of the present invention to make available amidines having an improved fungicidal effectiveness.

The object has been achieved, surprisingly, using thiadiazolyloxyphenylamidines of the formula (I)

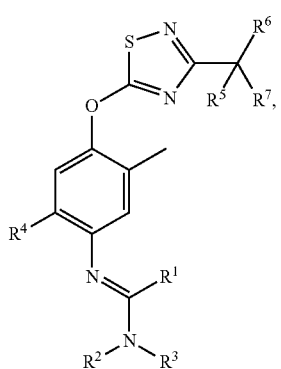

(I)

in which $R^1$ is chosen from hydrogen; linear or branched $C_{1-12}$-alkyl, $C_{2-12}$-alkenyl or $C_{2-12}$-alkynyl or cyclic $C_{3-8}$-alkyl, $C_{4-8}$-alkenyl or $C_{4-8}$-alkynyl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' being hydrogen or a $C_{1-12}$-alkyl group; —SH; —SR", R" being a $C_{1-12}$-alkyl group which can be substituted with one or more groups chosen from —R', —X, —OR', —SR', —NR'$_2$, —SiR'$_3$, —COOR', —CN and —CONR$_2$', R' having the above meanings;

$R^2$ is chosen from linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR'$_2$, R' having the above meanings;

$R^3$ is chosen from —CN, —SH, —SR", —OR", —(C=O)—R", R" having the above meanings; linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR'$_2$, R' having the above meanings;

or in which $R^2$ and $R^3$, $R^2$ and $R^1$ or $R^1$ and $R^3$ can form, together with the atoms to which they are bonded or with additional atoms chosen from nitrogen, oxygen, phosphorus and sulphur, a four- to seven-membered ring which can be substituted with R', OR', SR', NR'$_2$ or SiR'$_3$ groups, R' having the above meanings;

$R^4$ is chosen from the group consisting of halogen (—X) and —CN;

$R^5$, $R^6$ and $R^7$ are chosen, independently of one another, from hydrogen, linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl groups or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', halogen (—X), alkoxy (—OR'), thioether or mercapto (—SR'), amino (—NR'$_2$), silyl (—SiR'$_3$), carboxyl (—COOR'), cyano (—CN) and amide (—CONR$_2$') groups, R' having the above meanings;

or $R^5$ and $R^6$, $R^6$ and $R^7$ or $R^5$ and $R^7$ can form, together with the carbon atom to which they are bonded or with additional atoms chosen from nitrogen, oxygen, phosphorus and sulphur, a three- to seven-membered ring which can be substituted with X, R', OR', SR', NR'$_2$, SiR'$_3$ C$_{15-18}$-aryl, C$_{7-19}$-aralkyl or C$_{7-19}$-alkaryl groups, R' having the above meanings and it being possible for the aryl, aralkyl or alkaryl groups to be substituted in the ring with X, R', OR' or SR' groups;

or

R$^5$ and R$^6$, R$^6$ and R$^7$ or R$^5$ and R$^7$ can form, together with the carbon atom to which they are bonded, a double bond which can be substituted with —CN, —SH, —SR", —OR", or —(C═O)—R", R" having the above meanings; or linear or branched C$_{1-12}$-alkyl, C$_{2-12}$-alkenyl or C$_{2-12}$-alkynyl, cyclic C$_{3-8}$-alkyl, C$_{4-8}$-alkenyl or C$_{4-8}$-alkynyl or C$_{5-18}$-aryl, C$_{7-19}$-aralkyl or C$_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

and the salts thereof.

DETAILED DESCRIPTION OF A PREFERRED EMBODIMENT

In connection with the present invention, the term halogens (X) comprises, unless otherwise defined, those elements which are chosen from the group consisting of fluorine, chlorine, bromine and iodine, fluorine, chlorine and bromine being preferably used and fluorine and chlorine being particularly preferably used.

Appropriately substituted groups can be mono- or polysubstituted, it being possible for the substituents in polysubstitutions to be identical or different.

Alkyl groups substituted with one or more halogen atoms (—X) are chosen, for example, from trifluoromethyl (CF$_3$), difluoromethyl (CHF$_2$), CF$_3$CH$_2$, ClCH$_2$, and CF$_3$CCl$_2$.

Alkyl groups in connection with the present invention are, unless otherwise defined, linear, branched or cyclic hydrocarbon groups which can optionally exhibit one, two or more single or double unsaturations or one, two or more heteroatoms chosen from oxygen, nitrogen, phosphorus and sulphur. In addition, the alkyl groups according to the invention can optionally be substituted by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR'$_2$) groups, R' being hydrogen or a C$_{1-12}$-alkyl group, preferably a C$_{2-10}$-alkyl group, particularly preferably a C$_{3-8}$-alkyl group, which can exhibit one or more heteroatoms chosen from nitrogen, oxygen, phosphorus and sulphur.

The definition C$_1$-C$_{12}$-alkyl comprises the biggest range defined herein for an alkyl group. Specifically, this definition comprises, for example, the meanings methyl, ethyl, n-propyl, isopropyl, n-butyl, isobutyl, sec-butyl and t-butyl, n-pentyl, n-hexyl, 1,3-dimethylbutyl, 3,3-dimethylbutyl, n-heptyl, n-nonyl, n-decyl, n-undecyl and n-dodecyl.

Alkenyl groups in connection with the present invention are, unless otherwise defined, linear, branched or cyclic hydrocarbon groups which comprise at least one single unsaturation (double bond) and can optionally exhibit one, two or more single or double unsaturations or one, two or more heteroatoms chosen from oxygen, nitrogen, phosphorus and sulphur. In addition, the alkenyl groups according to the invention can optionally be substituted by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR'$_2$) groups, R' being hydrogen or a C$_{1-12}$-alkyl group, preferably a C$_{2-10}$-alkyl group, particularly preferably a C$_{3-8}$-alkyl group, which can exhibit one or more heteroatoms chosen from nitrogen, oxygen, phosphorus and sulphur.

The definition C$_2$-C$_{12}$-alkenyl comprises the biggest range defined herein for an alkenyl group. Specifically, this definition comprises, for example, the meanings vinyl; allyl (2-propenyl), isopropenyl(1-methylethenyl); but-1-enyl(crotyl), but-2-enyl, but-3 -enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl, penta-1,3-dienyl.

Alkynyl groups in connection with the present invention are, unless otherwise defined, linear, branched or cyclic hydrocarbon groups which comprise at least one double unsaturation (triple bond) and can optionally exhibit one, two or more single or double unsaturations or one, two or more heteroatoms chosen from oxygen, nitrogen, phosphorus and sulphur. In addition, the alkynyl groups according to the invention can optionally be substituted by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR'$_2$) groups, R' being hydrogen or a linear, branched or cyclic C$_{1-12}$-alkyl group which can exhibit one or more heteroatoms chosen from nitrogen, oxygen, phosphorus and sulphur.

The definition C$_2$-C$_{12}$-alkynyl comprises the biggest range defined herein for an alkynyl group. Specifically, this definition comprises, for example, the meanings ethynyl (acetylenyl); prop-1-ynyl and prop-2-ynyl.

The definition C$_3$-C$_8$-cycloalkyl comprises monocyclic saturated hydrocarbon groups having 3 to 8 carbon ring members, such as cyclopropyl, cyclobutyl, cyclopentyl, cyclohexyl, cycloheptyl and cyclooctyl.

Aryl groups in connection with the present invention are, unless otherwise defined, aromatic hydrocarbon groups which can exhibit one, two or more heteroatoms chosen from oxygen, nitrogen, phosphorus and sulphur and can optionally be substituted by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide (—CONR$_2$') groups, R' being hydrogen or a C$_{1-12}$-alkyl group, preferably a C$_{2-10}$-alkyl group, particularly preferably a C$_{3-8}$-alkyl group, which can exhibit one or more heteroatoms chosen from nitrogen, oxygen, phosphorus and sulphur.

The definition C$_{5-18}$-aryl comprises the biggest range defined herein for an aryl group having 5 to 18 backbone atoms, it being possible for the carbon atoms to be exchanged for heteroatoms. Specifically, this definition comprises, for example, the meanings cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in connection with the present invention are, unless otherwise defined, alkyl groups substituted by aryl groups which can exhibit a $C_{1-8}$-alkylene chain and can be substituted in the aryl backbone or the alkylene chain by one or more heteroatoms chosen from oxygen, nitrogen, phosphorus and sulphur and optionally by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorus and sulphur.

The definition $C_{7-19}$-aralkyl group comprises the biggest range defined herein for an arylalkyl group with a total of 7 to 19 atoms in the backbone and alkylene chain. Specifically, this definition comprises, for example, the meanings benzyl and phenylethyl.

Alkylaryl groups (alkaryl groups) in connection with the present invention are, unless otherwise defined, aryl groups substituted by alkyl groups which can exhibit a $C_{1-8}$-alkyl chain and can be substituted in the aryl backbone or the alkyl chain by one or more heteroatoms chosen from oxygen, nitrogen, phosphorus and sulphur and optionally by additional groups chosen from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide (—CONR$_2$') groups, R' being hydrogen or a $C_{1-12}$-alkyl group, preferably a $C_{2-10}$-alkyl group, particularly preferably a $C_{3-8}$-alkyl group, which can exhibit one or more heteroatoms chosen from nitrogen, oxygen, phosphorus and sulphur.

The definition $C_{7-19}$-alkylaryl group comprises the biggest range defined herein for an alkylaryl group with a total of 7 to 19 atoms in the backbone and alkyl chain. Specifically, this definition comprises, for example, the meanings tolyl-, 2,3-, 2,4-, 2,5-, 2,6-, 3,4- or 3,5-dimethylphenyl.

The alkyl, alkenyl, alkynyl, aryl, alkylaryl and aralkyl groups can furthermore exhibit one or more heteroatoms which, unless otherwise defined, are chosen from nitrogen, oxygen, phosphorus and sulphur. The heteroatoms in this connection replace the carbon atoms indicated.

The compounds according to the invention can exist, if appropriate, as mixtures of different possible isomeric forms, in particular of stereoisomers, such as, e.g., E- and Z-isomers, threo- and erythro-isomers, and optical isomers, but, if appropriate, also tautomers. Both the E- and Z-isomers, as also the threo- and erythro-isomers, and also the optical isomers, any mixture of these isomers, and the possible tautomeric forms, are disclosed and claimed.

The amidines according to the invention are compounds of the formula (I)

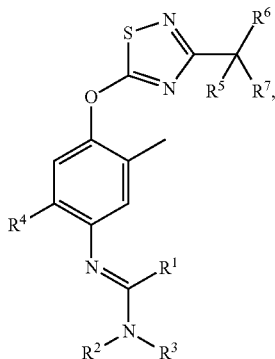

or the salts, N-oxides and metal complexes thereof and the stereoisomers thereof.

In formula (I), the groups have the meanings defined below. The definitions met with are valid for all intermediates equally:

in which $R^1$ is chosen from hydrogen; linear or branched $C_{1-12}$-alkyl, $C_{2-12}$-alkenyl or $C_{2-12}$-alkynyl or cyclic $C_{3-8}$-alkyl, $C_{4-8}$-alkenyl or $C_{4-8}$-alkynyl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR'$_2$, R' being hydrogen or a $C_{1-12}$-alkyl group; —SH; —SR'', R'' being a $C_{1-12}$-alkyl group which can be substituted with one or more groups chosen from —R', —X, —OR', —SR', —NR'$_2$, —SiR'$_3$, —COOR', —CN and —CONR$_2$', R' having the above meaning;

$R^2$ is chosen from linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

$R^3$ is chosen from —CH, —SH, —SR'', —OR'', —(C=O)—R'', R'' having the above meanings; linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

In an alternative embodiment according to the invention, $R^2$ and $R^3$, $R^2$ and $R^1$ or $R^1$ and $R^3$ can form, together with the atoms to which they are bonded, or with additional atoms chosen from nitrogen, oxygen, phosphorus and sulphur, a four- to seven-membered ring which can be substituted with R', OR', SR', NR'$_2$ or SiR'$_3$ groups, R' having the above meanings;

$R^4$ is chosen from the group consisting of halogen (—X) and —CN;

$R^5$, $R^6$ and $R^7$ are chosen, independently of one another, from hydrogen, linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', halogen (—X), alkoxy (—OR'), thioether or mercapto (—SR'), amino (—NR'$_2$), silyl (—SiR'$_3$), carboxyl (—COOR'), cyano (—CN) and amide (—CONR'$_2$) groups, R' have the above meanings;

In an alternative embodiment of the invention, $R^5$ and $R^6$, $R^6$ and $R^7$ or $R^5$ and $R^7$ can form, together with the carbon atom to which they are bonded or with additional atoms chosen from nitrogen, oxygen, phosphorus and sulphur, a three- to seven-membered ring which can be substituted with X, R', OR', SR', NR'$_2$, SiR'$_3$, $C_{5-18}$-aryl, $C_{7-19}$-aralkyl or $C_{7-19}$-alkaryl groups, R' having the above meanings and it being possible for the aryl, aralkyl or alkaryl groups to be in turn substituted in the ring with X, R', OR' or SR' groups;

In an additional alternative embodiment of the invention, $R^5$ and $R^6$, $R^6$ and $R^7$ and $R^5$ and $R^7$ can form, together with the carbon atom to which they are bonded, a double bond. The double bond can be substituted with —CN, —SH, —SR", OR" or (C=O)—R", R" having the above meanings; or linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

and the salts thereof.

The respective groups $R^5$, $R^6$ or $R^7$ not participating in the formation of the ring or of the double bond correspond to the definition met with above.

In formula (I), the groups have the preferred meanings defined below. The definitions met with as preferred are valid for all intermediates equally:

$R^1$ is chosen from the group consisting of hydrogen, a mercapto group (—SH) or $C_{1-8}$-alkyl groups;

$R^2$ is chosen from linear or branched $C_{1-8}$-alkyl groups;

$R^3$ is chosen from linear, branched and alicyclic $C_{1-8}$-alkyl groups;

In an alternative preferred embodiment according to the invention, $R^2$ and $R^3$ can form, together with the nitrogen atom to which they are bonded or with additional atoms chosen from nitrogen and oxygen, a five- or six-membered ring which can be substituted with one or more $C_{1-12}$-alkyl groups;

$R^4$ is chosen from the group consisting of F, Cl, Br and I;

$R^5$ and $R^6$ are chosen, independently of one another, from hydrogen and linear $C_{1-8}$-alkyl groups;

$R^7$ is chosen from the group consisting of hydrogen, linear, branched, alicyclic or heterocyclic $C_{1-12}$-alkyl groups, halogen atoms, $C_{1-4}$-haloalkyl groups, phenyl groups and benzyl groups, it being possible for the phenyl or benzyl groups to be substituted with one or more groups chosen from —R', —X, —OR', —SR', —NR'$_2$, —SiR'$_3$, —COOR', —CN and —CONR$_2$';

In an alternative preferred embodiment of the invention, $R^5$ and $R^6$ can form, together with the carbon atom to which they are bonded or with additional atoms chosen from nitrogen, oxygen, phosphorus and sulphur, a three-, four- or five-membered ring which can be substituted with X, R' or phenyl groups, R' having the above meanings. In this embodiment, the radical $R^7$ is chosen from hydrogen, halogen atoms, phenyl groups, phenoxy groups and benzyl groups, it being possible for the abovementioned groups to be substituted by one, two or more halogen atoms.

In an additional preferred embodiment, $R^5$ and $R^6$ form, together with the carbon atom to which they are bonded, a double bond. The double bond can be substituted with hydrogen, linear or branched $C_{1-12}$-alkyl or cyclic $C_{3-8}$-alkyl groups, halogen atoms, $C_{1-4}$-haloalkyl groups, phenyl groups and benzyl groups, it being possible for the abovementioned phenyl or benzyl groups to be substituted in turn with one or more groups chosen from —R', —X, —OR', —SR', —NR'$_2$, —SiR'$_3$, —COOR', —CN and —CONR'$_2$. In this embodiment, a radical $R^7$ is chosen from hydrogen and $C_{1-4}$-alkyl.

In formula (I), the radicals have the particularly preferred meanings defined below. The definitions met with as particularly preferred are valid for all intermediates equally:

$R^1$ is chosen from the group consisting of hydrogen, mercapto and methyl;

$R^2$ is chosen from the group consisting of methyl and ethyl;

$R^3$ is chosen from the group consisting of methyl, ethyl and isopropyl;

In an alternative particularly preferred embodiment according to the invention, $R^2$ and $R^3$ form, together with the nitrogen atom to which they are bonded, a piperidyl, pyrrolidyl or 2,6-dimethylmorpholinyl radical;

$R^4$ is chosen from the group consisting of Cl and Br;

$R^5$ and $R^6$ are chosen, independently of one another, from hydrogen, methyl groups and ethyl groups;

$R^7$ is chosen from the group consisting of methyl, methoxy, ethoxy, trimethylsilyl, triethylsilyl, phenyl, benzyl, 4-chlorobenzyl, 4-chlorophenyl, 4-bromophenyl, 2,4-dichlorophenyl, 2-chlorophenoxy, 3-chlorophenoxy, 4-chlorophenoxy and 3-trifluoromethyl groups.

In an alternative particularly preferred embodiment according to the invention, $R^5$ and $R^6$ form, together with the carbon atom to which they are bonded, a cyclopropyl ring which can be substituted with one or two chloro or bromo atoms or with a phenyl or halophenyl group. In this embodiment, the radical $R^7$ is chosen from halogen, preferably chlorine, and phenyl or benzyl groups which can be substituted with halogen atoms, preferably with chlorine.

In an additional particularly preferred embodiment according to the invention, $R^5$ and $R^6$ form, together with the carbon atom to which they are bonded, a double bond which can be substituted with a 4-fluorophenyl group. In this embodiment, the radical $R^7$ is chosen from hydrogen or $C_{1-4}$-alkyl. In other words, the thiadiazolyl radical is substituted in the 3-position with a 4-fluorobenzylidene group.

The present invention also relates in addition to the salts, N-oxides and metal complexes of the compounds described above and to the stereoisomers thereof.

Depending on the type of the substituents defined above, the compounds of the formula (I) exhibit acidic or basic properties and can form salts with inorganic or organic acids or with bases or with metal ions, if appropriate also internal salts or adducts.

Suitable as metal ions are in particular the ions of the elements of the second main group, in particular calcium and magnesium, of the third and fourth main groups, in particular aluminium, tin and lead, and also of the first to eighth subgroups, in particular chromium, manganese, iron, cobalt, nickel, copper, zinc and others. Particular preference is given to the metal ions of the elements of the fourth period. The metals can in this connection exist in the different valences befitting them.

If the compounds of the formula (I) carry hydroxyl, carboxyl or other groups which induce acidic properties, these compounds can be reacted with bases to give salts.

Suitable bases are, for example, hydroxides, carbonates or hydrogencarbonates of alkali or alkaline earth metals, in particular those of sodium, potassium, magnesium and calcium, furthermore ammonia, primary, secondary and tertiary amines with $(C_1-C_4)$-alkyl groups, mono-, di- and trialkanolamines of $(C_1-C_4)$-alkanols, choline and cholincholine.

If the compounds of the formula (I) carry amino, alkylamino or other groups which induce basic properties, these compounds can be reacted with acids to give salts.

Examples of inorganic acids are hydrohalides, such as hydrogen fluoride, hydrogen chloride, hydrogen bromide and hydrogen iodide, sulphuric acid, phosphoric acid and nitric acid and acid salts, such as $NaHSO_4$ and $KHSO_4$.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids with straight-chain or branched alkyl groups having 1 to 20 carbon atoms), arylsulphonic acids or aryldisulphonic acids (aromatic groups, such as phenyl and naphthyl, which carry one or two sulphonic acid groups), alkylphosphonic acids (phosphonic acids with straight-chain or branched alkyl groups having 1 to 20 carbon atoms) and arylphosphonic or aryldiphosphonic acids (aromatic radicals, such as phenyl and naphthyl, which carry one or two phosphonic acid groups), it being possible for the alkyl or aryl groups to carry additional substituents, e.g. p-toluenesulphonic acid, salicylic acid, p-aminosalicylic acid, 2-phenoxybenzoic acid, 2-acetoxybenzoic acid, and the like.

The salts thus obtained likewise exhibit fungicidal, insecticidal or herbicidal properties.

In connection with the present invention, amidines are particularly preferably chosen from the group consisting of: N'-{4-[(3-(tert-butyl)-1,2,4-thiadiazol-5-yl)oxy]-2-chloro-5-methylphenyl}-N-ethyl-N-methylimidoformamide (Example 1); N'-{2-bromo-4-[(3-(tert-butyl)-1,2,4-thiadiazol-5-yl)oxy]-5-methylphenyl}-N-ethyl-N-methylimidoformamide (Example 2); N'-(2-chloro-4-{[3-(1-chlorocyclopropyl)-1,2,4-thiadiazol-5-yl]oxy}-5-methylphenyl)-N-ethyl-N-methylimidoformamide (Example 3); N'-(2-chloro-4-{[3-(1-chlorocyclopropyl)-1,2,4-thiadiazol-5-yl]oxy}-5-methylphenyl)-N-methyl-N-propan-2-ylimidoformamide (Example 4); 2-chloro-4-{[3-(1-chlorocyclopropyl)-1,2,4-thiadiazol-5-yl]oxy}-5-methyl-N-[(E)-piperidin-1-ylmethylidene]aniline (Example 5); N'-[2-chloro-4-({3-[1-(4-chlorophenyl)ethyl]-1,2,4-thiadiazol-5-yl}oxy)-5-methylphenyl]-N-ethyl-N-methylimidoformamide (Example 6); 2-chloro-4-({3-[1-(4-chlorophenyl)ethyl]-1,2,4-thiadiazol-5-yl}oxy)-5-methyl-N-[(E)-piperidin-1-ylmethylidene]aniline (Example 7); N'-[2-chloro-4-({3-[1-(4-chlorophenyl)ethyl]-1,2,4-thiadiazol-5-yl}oxy)-5-methylphenyl]-N-methyl-N-(propan-2-yl)imidoformamide (Example 8); N'-[2-chloro-4-({3-[2-(4-chlorophenyl)ethyl]-1,2,4-thiadiazol-5-yl}oxy)-5-methylphenyl]-N-ethyl-N-methylimidoformamide (Example 9); 2-chloro-4-({3-[2-(4-chlorophenyl)ethyl]-1,2,4-thiadiazol-5-yl}oxy)-5-methyl-N-[(Z)-piperidin-1-ylmethylidene]aniline (Example 10); N'-[2-chloro-4-({3-[2-(4-chlorophenyl)propan-2-yl]-1,2,4-thiadiazol-5-yl}oxy)-5-methylphenyl]-N-ethyl-N-methylimidoformamide (Example 11); 2-chloro-4-({3-[2-(4-chlorophenyl)propan-2-yl]-1,2,4-thiadiazol-5-yl}oxy)-5-methyl-N-[(Z)-piperidin-1-ylmethylidene]aniline (Example 12); N'-[2-chloro-4-({3-[2-(4-chlorophenyl)propan-2-yl]-1,2,4-thiadiazol-5-yl}oxy)-5-methylphenyl]-N-methyl-N-(propan-2-yl)imidoformamide (Example 13); N'-{4-[(3-benzyl-1,2,4-thiadiazol-5-yl)oxy]-2-chloro-5-methylphenyl}-N-ethyl-N-methylimidoformamide (Example 14); N'-[2-chloro-4-({3-[(E)-2-(4-fluorophenyl)ethenyl]-1,2,4-thiadiazol-5-yl}oxy)-5-methylphenyl]-N-ethyl-N-methylimidoformamide (Example 15); 2-chloro-4-({3-[(E)-2-(4-fluorophenyl)ethenyl]-1,2,4-thiadiazol-5-yl}oxy)-5-methyl-N-[(Z)-piperidin-1-ylmethylidene]aniline (Example 16); N'-[2-chloro-4-({3-[1-(4-chlorophenyl)cyclopropyl]-1,2,4-thiadiazol-5-yl}oxy)-5-methylphenyl]-N-ethyl-N-methylimidoformamide (Example 17); N'-(2-chloro-4-{[3-(4-chlorobenzyl)-1,2,4-thiadiazol-5-yl]oxy}-5-methylphenyl)-N-ethyl-N-methylimidoformamide (Example 18); N'-(2-chloro-4-{[3-(chloromethyl)-1,2,4-thiadiazol-5-yl]oxy}-5-methylphenyl)-N-ethyl-N-methylimidoformamide (Example 19); N'-[2-chloro-4-({3-[1-(4-chlorophenyl)cyclopropyl]-1,2,4-thiadiazol-5-yl}oxy)-5-methylphenyl]-N-methyl-N-(propan-2-yl)imidoformamide (Example 20); 2-chloro-4-({3-[1-(4-chlorophenyl)cyclopropyl]-1,2,4-thiadiazol-5-yl}oxy)-5-methyl-N-[(Z)-piperidin-1-ylmethylidene]aniline (Example 21); N'-[2-chloro-4-({3-[(4-chlorophenoxy)methyl]-1,2,4-thiadiazol-5-yl}oxy)-5-methylphenyl]-N-ethyl-N-methylimidoformamide (Example 22); N'-[2-chloro-4-({3-[(E)-2-(4-fluorophenyBethenyl]-1,2,4-thiadiazol-5-yl}oxy)-5-methylphenyl]-N-methyl-N-(propan-2-yl)imidoformamide (Example 23); N'-{4-[(3-(tert-butyl)-1,2,4-thiadiazol-5-yl)oxy]-2-chloro-5-methylphenyl}-N-methyl-N-propylimidoformamide (Example 24); N'-{4-[(3-(tert-butyl)-1,2,4-thiadiazol-5-yl)oxy]-2-chloro-5-methylphenyl}-N-methyl-N-(prop-2-en-1-yl)imidoformamide (Example 25); N'-{4-[(3-(tert-butyl)-1,2,4-thiadiazol-5-yl)oxy]-2-chloro-5-methylphenyl}-N-(cyclopropylmethyl)-N-methylimidoformamide (Example 26); N'-{4-[(3-(tert-butyl)-1,2,4-thiadiazol-5-yl)oxy]-2-chloro-5-methylphenyl}-N-(3-methoxypropyl)-N-methylimidoformamide (Example 27); N'-(2-chloro-5-methyl-4-{[3-(2-methyl-1-phenylpropan-2-yl)-1,2,4-thiadiazol-5-yl]oxy}phenyl)-N-ethyl-N-methylimidoformamide (Example 28); rel-N'-[2-chloro-5-methyl-4-({3-[(1R,2R)-2-phenylcyclopropyl]-1,2,4-thiadiazol-5-yl}oxy)phenyl]-N-ethyl-N-methylimidoformamide (Example 29); rel-2-chloro-5-methyl-4-{3-[(1R,2R)-2-phenylcyclopropyl]-1,2,4-thiadiazol-5-yl}oxy)-N-[(E)-piperidin-1-ylmethylidene]aniline (Example 30); rel-N'-[2-chloro-5-methyl-4-({3-[(1R,2R)-2-phenylcyclopropyl]-1,2,4-thiadiazol-5-yl}oxy)phenyl]-N-methyl-N-(propan-2-yl)imidoformamide (Example 31); N'-(2-chloro-4-{[3-(2,2-dichloro-1-methylcyclopropyl)-1,2,4-thiadiazol-5-yl]oxy}-5-methylphenyl)-N-ethyl-N-methylimidoformamide (Example 32); N'-(4-{[3-(4-bromobenzyl)-1,2,4-thiadiazol-5-yl]oxy}-2-chloro-5- methylphenyl)-N-ethyl-N-methylimidoformamide (Example 33); N'-[2-chloro-5-methyl-4-({3-[3-(trifluoromethyl)benzyl]-1,2,4-thiadiazol-5-yl}oxy)phenyl]-N-ethyl-N-methylimidoformamide (Example 34); N'-[2-chloro-4-({3-[(3-chlorophenoxy)methyl]-1,2,4-thiadiazol-5-yl}oxy)-5-methylphenyl]-N-ethyl-N-methylimidoformamide (Example 35); N'-[2-chloro-4-({3-[(2-chlorophenoxy)methyl]-1,2,4-thiadiazol-5-yl}oxy)-5-methylphenyl]-N-ethyl-N-methylimidoformamide (Example 36); N'-(2-chloro-5-methyl-4-{[3-(phenoxymethyl)-1,2,4-thiadiazol-5-yl]oxy}phenyl)-N-ethyl-N-methylimidoformamide (Example 37); N'-(2-chloro-4-{[3-(2,4-dichlorobenzyl)-1,2,4-thiadiazol-5-yl]oxy}-5-methylphenyl)-N-ethyl-N-methylimidoformamide (Example 38); N'-(2-chloro-4-{[3-(1-chloro-2-methylpropan-2-yl)-1,2,4-thiadiazol-5-yl]oxy}-5-methylphenyl)-N-ethyl-N-methylimidoformamide (Example 39); N'-(2-chloro-4-{[3-(2,4-difluorobenzyl)-1,2,4-thiadiazol-5-yl]oxy}-5-methylphenyl)-N-ethyl-N-methylimidoformamide (Example 40).

Preparation of the Amidines According to the Invention

The amidines according to the invention can be obtained by the process represented in the following Schemes (Ia) and (Ib):

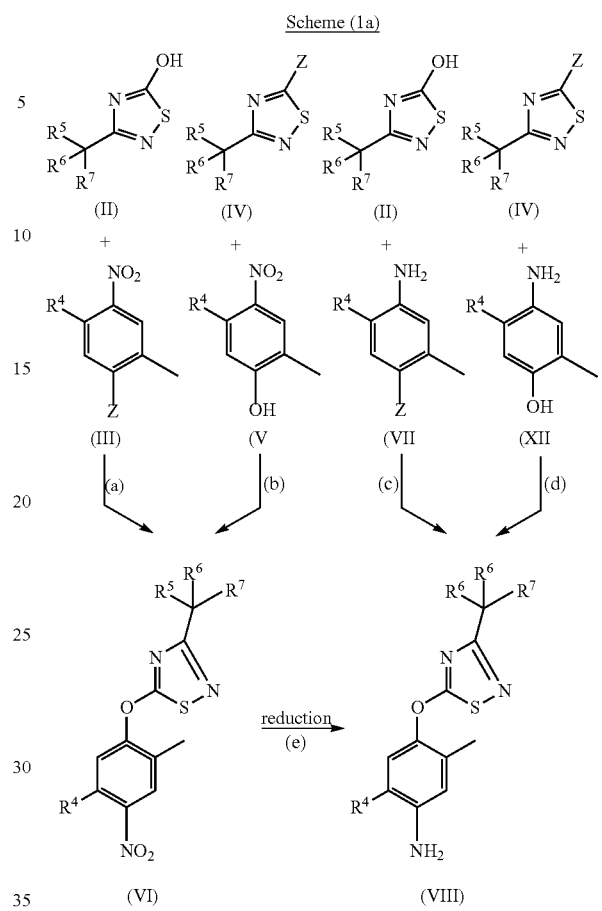

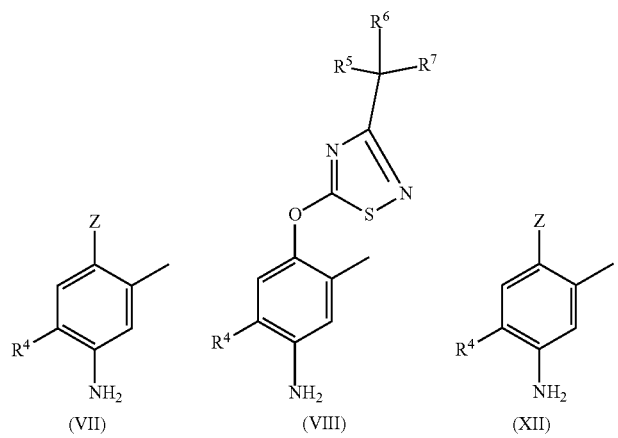

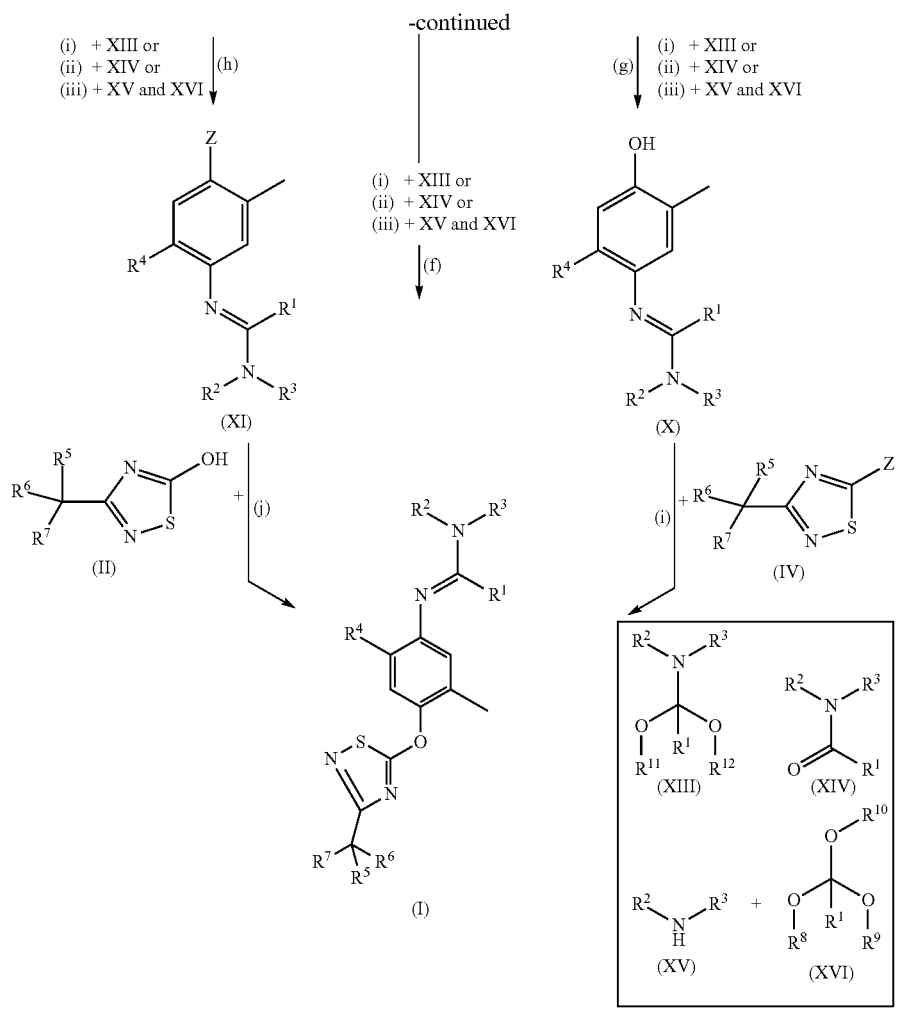

Stage (a)

In an embodiment according to the invention, nitrobenzene derivatives of the formula (III) are reacted with thiadiazolyl alcohols of the formula (II) or the alkoxides formed therefrom according to the following reaction scheme to give nitrophenyl ethers of the formula (VI):

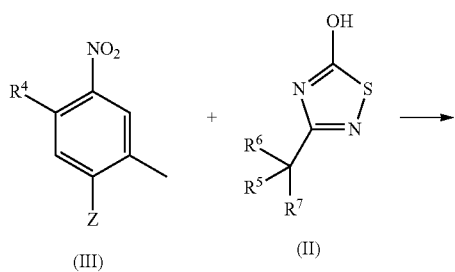

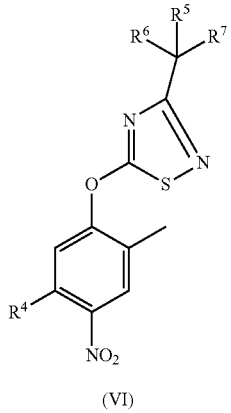

All substituents are suitable as leaving group Z which exhibit a satisfactory nucleofugality under the prevailing reaction conditions. Mention may be made, as suitable leaving groups, for example, of halogens, triflate, mesylate, tosylate or $SO_2Me$.

The nitrobenzene derivatives of the formula (III) can be obtained in accordance with the Journal of the Chemical Society, 1926, 2036.

The reaction preferably takes place in the presence of a base.

Suitable bases are organic and inorganic bases which are normally used in such reactions. Use is preferably made of bases which, for example, are chosen from the group consisting of hydrides, hydroxides, amides, alkoxides, acetates, fluorides, phosphates, carbonates and hydrogencarbonates of alkali metals or alkaline earth metals. Particular preference is given in this connection to sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate and caesium carbonate. Furthermore, tertiary amines, such as, e.g., trimethylamine, triethylamine, tributylamine, N,N-dimethylaniline, N,N-dimethylbenzylamine, pyridine, N-methylpiperidine, N-methylpyrrolidone, N,N-dimethylaminopyridine, diazabicyclooctane (DABCO), diazabicyclononene (DBN) and diazabicycloundecene (DBU), are.

If appropriate, a catalyst chosen from the group consisting of palladium, copper and the salts or complexes thereof can be used.

The reaction of the nitrobenzene derivative with the phenol can be carried out neat or in a solvent; preferably, the reaction is carried out in a solvent which is chosen from standard solvents which are inert under the prevailing reaction conditions.

Preference is given to aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, e.g., chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n-butyronitrile, isobutyronitrile or benzonitrile; amides, such as, for example, N,N-dimethylformamide (DMF), N,N-dimethylacetamide, N-methylformanilide, N-methylpyrrolidone (NMP) or hexamethylphosphoramide; or mixtures of these with water, and also pure water.

The reaction can be carried out under vacuum, at standard pressure or under an excess pressure and at temperatures of $-20$ to $200°$ C.; preferably, the reaction is carried out at standard pressure and temperatures from 50 to $150°$ C.

Stage (b)

In an alternative embodiment according to the invention, nitrophenol derivatives of the formula (V) or the phenoxides formed therefrom are reacted with thiadiazolyl derivatives of the formula (IV) according to the following reaction scheme to give nitrophenyl ethers of the formula (VI):

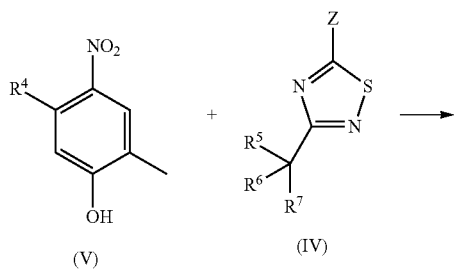

(V)            (IV)

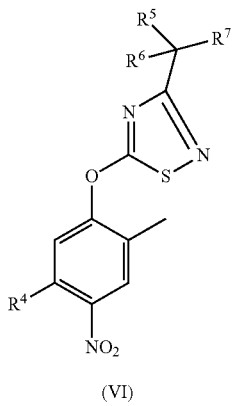

(VI)

The nitrophenol derivatives of the formula (V) can be obtained in accordance with the Journal of the Chemical Society, 1926, 2036.

With regard to the reaction conditions, solvents, catalysts and suitable leaving groups, reference may be made to stage (a).

Stage (c)

In an additional alternative embodiment according to the invention, anilines of the formula (VII) are reacted with thiadiazolyl alcohols of the formula (II) or the alkoxides formed therefrom according to the following reaction scheme to give aminophenyl ethers of the formula (VIII):

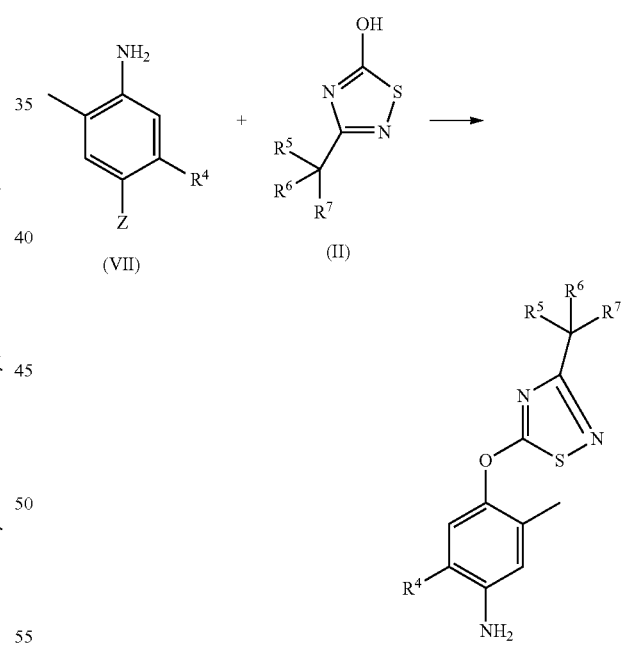

With regard to the reaction conditions, solvents, catalysts and suitable leaving groups, reference may be made to stage (a).

Stage (d)

In an additional alternative embodiment according to the invention, aminophenols of the formula (XII) are reacted with thiadiazolyl derivatives of the formula (IV) according to the following reaction scheme to give aminophenyl ethers of the formula (VIII):

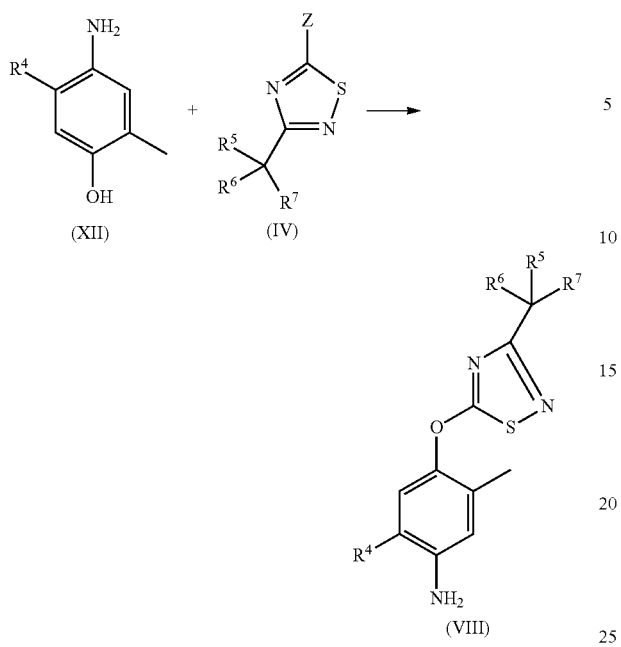

With regard to the reaction conditions, solvents, catalysts and suitable leaving groups, reference may be made to stage (a) and stage (c).

Stage (e)

The nitrophenyl ethers of the formula (VI) obtained in stages (a) and (b) can be reduced according to the following reaction scheme to give the aniline ethers of the formula (VIII):

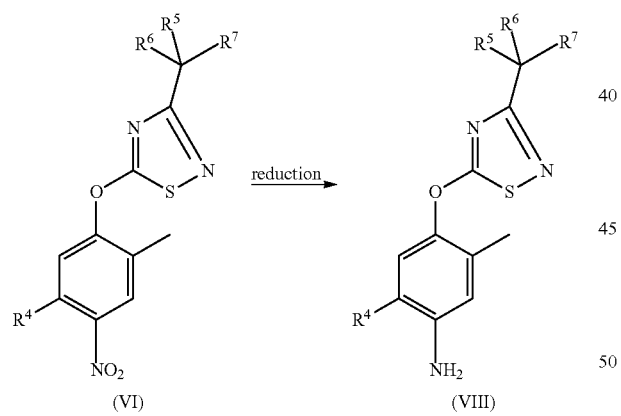

The reduction according to stage (e) can be carried out using all the methods described in the state of the art for the reduction of nitro groups.

The reduction is preferably carried out with tin chloride in concentrated hydrochloric acid, as described in WO-A-0 046 184. Alternatively, the reduction can, however, also be carried out with hydrogen gas, if appropriate in the presence of suitable hydrogenation catalysts, such as, e.g., Raney nickel or Pd/C. The reaction conditions are previously described in the state of the art and are familiar to a person skilled in the art.

If the reduction is carried out in the liquid phase, the reaction is to take place in a solvent which is inert with regard to the prevailing reaction conditions. Such as toluene, for example.

Stage (f)

The reaction according to stage (f) of the aniline ethers of the formula (VIII) to give the amidines of the formula (I) according to the invention can be carried out, as represented above in Scheme (I), according to different alternative processes using (i) aminoacetals of the formula (XIII) or
(ii) amides of the formula (XIV) or
(iii) amines of the formula (XV) in the presence of orthoesters of the formula (XVI), according to the following reaction scheme:

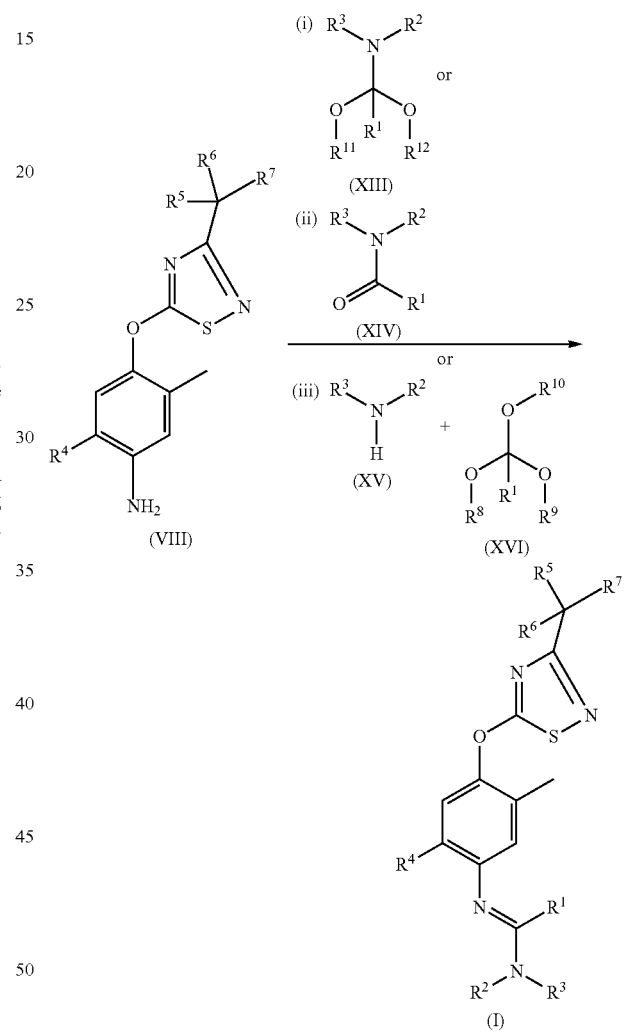

The individual alternative embodiments (i) to (iii) of the process according to the invention are to be briefly explained below:

(i) According to an embodiment according to the invention which is represented in Scheme (I) as stage (i), the aniline ethers of the formula (VIII) are reacted with aminoacetals of the formula (XIII), in which $R^1$, $R^2$ and $R^3$ are as defined above and $R^{11}$ and $R^{12}$ are chosen from $C_{1-8}$-alkyl groups, preferably from $C_{2-6}$-alkyl groups, particularly preferably from $C_{3-5}$-alkyl groups, and can form, together with the oxygen atoms to which they are bonded, a five- or six-membered ring, to give the thiadiazolyloxyphenylamidines of the formula (I) according to the invention.

The aminoacetals of the formula (XIII) can be obtained from the formamides described in JACS, 65, 1566 (1943), by reaction with alkylating reagents, such as, e.g., dimethyl sulphate.

The reaction according to stage (i) preferably takes place in the presence of an acid.

Suitable acids are, for example, chosen from the group consisting of organic and inorganic acids, p-toluenesulphonic acid, methanesulphonic acid, hydrochloric acid (gaseous, aqueous or in organic solution) or sulphuric acid being.

(ii) In an alternative embodiment according to the invention which is represented in Scheme (I) as stage (ii), the aniline ethers of the formula (VIII) are reacted with amides of the formula (XIV), in which the $R^1$, $R^2$ and $R^3$ groups are as defined above, to give the thiadiazolyloxyphenylamidines according to the invention.

The reaction according to stage (ii) takes place, if appropriate, in the presence of a halogenating agent. Suitable halogenating agents are, for example, chosen from the group consisting of $PCl_5$, $PCl_3$, $POCl_3$ or $SOCl_2$.

Moreover, the reaction can alternatively be carried out in the presence of a coupling agent.

Suitable coupling agents are those which are normally used to connect amide bonds; mention may be made, for example, of compounds which form acid halides, such as, e.g., phosgene, phosphorous tribromide, phosphorous trichloride, phosphorous pentachloride, phosphoryl chloride or thionyl chloride; compounds which form anhydrides, such as, e.g., chloroformate, methyl chloroformate, isopropyl chloroformate, isobutyl chloroformate or methanesulphonyl chloride; carbodiimides, such as, e.g., N,N'-dicyclohexylcarbodiimide (DCC), or other standard coupling agents, such as, e.g., phosphorous pentoxide, polyphosphoric acid, N,N'-carbodiimidazole, 2-ethoxy-N-ethoxycarbonyl-1,2-dihydroquinoline (EEDQ), triphenylphosphine/tetrachloromethane or bromotripyrrolidinophosphonium hexafluorophosphate.

The reaction according to stage (ii) preferably takes place in a solvent which is chosen from the normal solvents which are inert under the prevailing reaction conditions. Use is preferably made of aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, e.g., chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n-butyronitrile, isobutyronitrile or benzonitrile; amides, such as, for example, N,N-dimethylformamide (DMF), N,N-dimethylacetamide, N-methylformanilide, N-methylpyrrolidone (NMP) or hexamethylphosphoramide; esters, such as, for example, methyl or ethyl acetate; sulphoxides, such as, for example, dimethyl sulphoxide (DMSO); sulphones, such as, for example, sulpholane; alcohols, such as, for example, methanol, ethanol, n-propanol, isopropanol, n-butanol, isobutanol, sec-butanol, tert-butanol, ethanediol, 1,2-propanediol, ethoxyethanol, methoxyethanol, diethylene glycol monomethyl ether, diethylene glycol monoethyl ether or mixtures of these.

(iii) According to an additional alternative embodiment according to the invention which is represented in Scheme (I) as stage (iii), the aniline ethers of the formula (VIII) are reacted with amines of the formula (XV), in which the $R^2$ and $R^3$ groups are as defined above, in the presence of orthoesters of the formula (XVI), in which $R^1$ is hydrogen and $R^8$ to $R^{10}$ are chosen, independently of one another, from $C_{1-8}$-alkyl groups, preferably from $C_{2-6}$-alkyl groups, particularly preferably from $C_{3-5}$-alkyl groups, and can form, together with the oxygen atoms to which they are bonded, a five- or six-membered ring, to give the thiadiazolyloxyphenylamidines according to the invention.

The reaction according to stage (iii) preferably takes place in a solvent which is chosen from the normal solvents which are inert under the prevailing reaction conditions. Use is preferably made of aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, e.g., chlorobenzene, dichlorobenzene, dichloromethane, chloroform, carbon tetrachloride, dichloroethane or trichloroethane; ethers, such as, for example, diethyl ether, diisopropyl ether, methyl tert-butyl ether (MTBE), methyl tert-amyl ether, dioxane, tetrahydrofuran, 1,2-dimethoxyethane, 1,2-diethoxyethane or anisole; nitriles, such as, for example, acetonitrile, propionitrile, n-butyronitrile, isobutyronitrile or benzonitrile; amides, such as, for example, N,N-dimethylformamide (DMF), N,N-dimethylacetamide, N-methylformanilide, N-methylpyrrolidone (NMP) or hexamethylphosphoramide; esters, such as, for example, methyl or ethyl acetate; sulphoxides, such as, for example, dimethyl sulphoxide (DMSO); sulphones, such as, for example, sulpholane; alcohols, such as, for example, methanol, ethanol, n-propanol, isopropanol, n-butanol, isobutanol, sec-butanol, tert-butanol, ethanediol, 1,2-propanediol, ethoxyethanol, methoxyethanol, diethylene glycol monomethyl ether, diethylene glycol monoethyl ether; or mixtures of these with water and also pure water.

Stage (g)

In an alternative embodiment according to the invention, the aminophenols of the formula (XII) can even be reacted (i) with aminoacetals of the formula (XIII) or
(ii) with amides of the formula (XIV) or
(iii) with amines of the formula (XV) in the presence of orthoesters of the formula (XVI), according to the following reaction scheme, to give amidines of the formula (X):

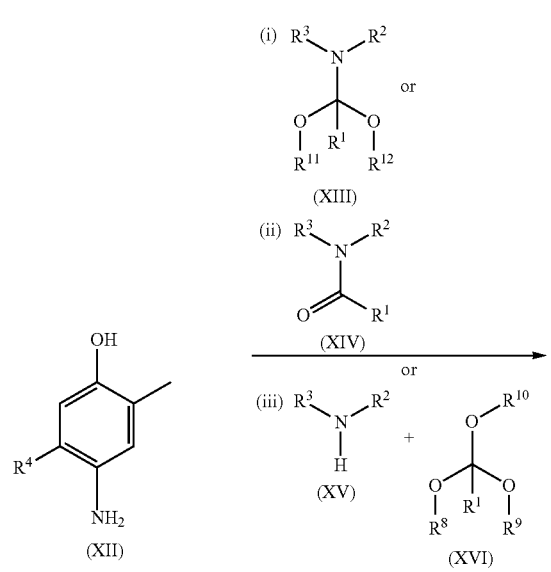

-continued

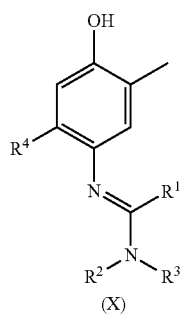

With regard to the reaction conditions, solvents and catalysts, reference may be made to stage (f).

The further reaction of the amidines of the formula (X) to give the target molecules of the formula (I) according to the invention can be carried out, for example, as described in stage (j).

Stage (h)

In an alternative embodiment according to the invention, the aminophenyl derivatives of the formula (VII) can be reacted
(i) with aminoacetals of the formula (XIII) or
(ii) with amides of the formula (XIV) or
(iii) with amines of the formula (XV) in the presence of orthoesters of the formula (XVI)
according to the following reaction scheme, to give amidines of the formula (XI):

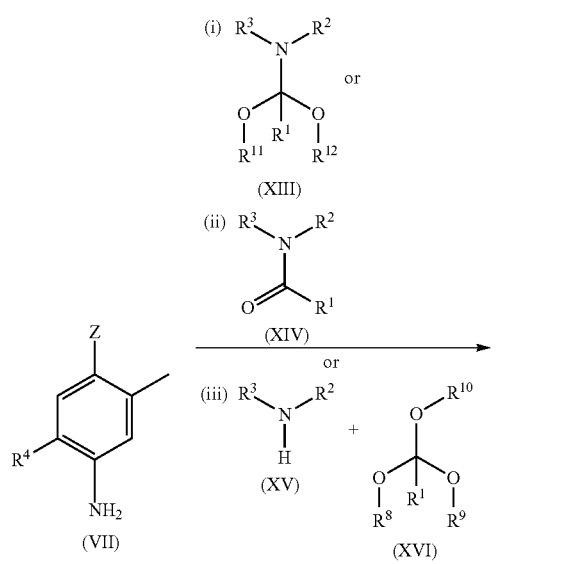

With regard to the reaction conditions, solvents and catalysts, reference may be made to stage (f).

The further reaction of the amidines of the formula (XI) to give the target molecules of the formula (I) according to the invention can be carried out, for example, as described in stage (i).

Stage (i)

According to an additional embodiment according to the invention, the amidines of the formula (XI) which can be obtained from stage (h) can be reacted according to the following reaction scheme with thiadiazolyl alcohols or the alkoxides formed therefrom to give the target molecules of the formula (I) according to the invention:

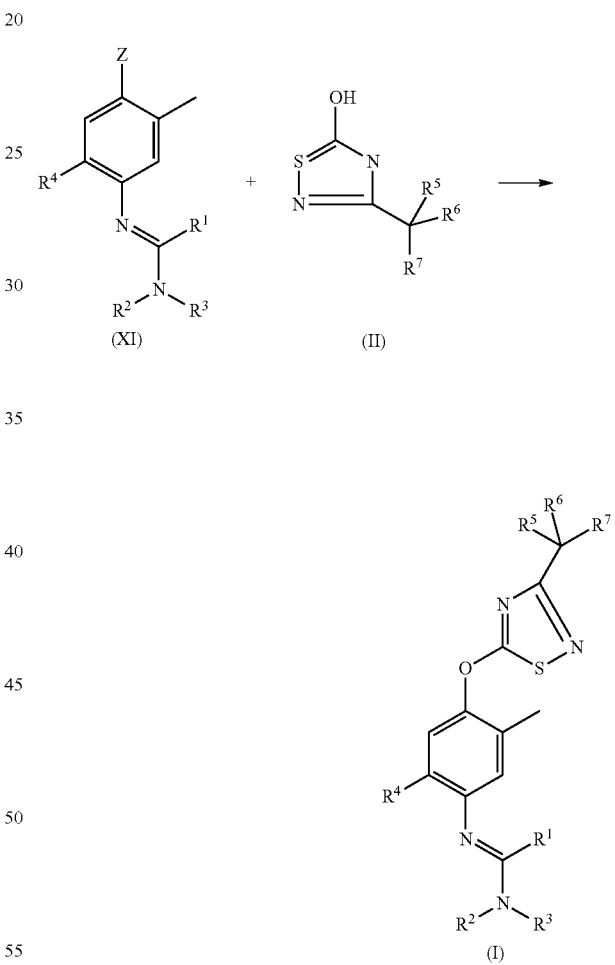

With regard to the reaction conditions, solvents and catalysts, reference may be made to stage (f).

Stage (j)

According to a further embodiment according to the invention, the amidines of the formula (X) which can be obtained from stage (g) can be reacted according to the following reaction scheme with thiadiazolyl derivatives of the formula (IV) to give the target molecules of the formula (I) according to the invention:

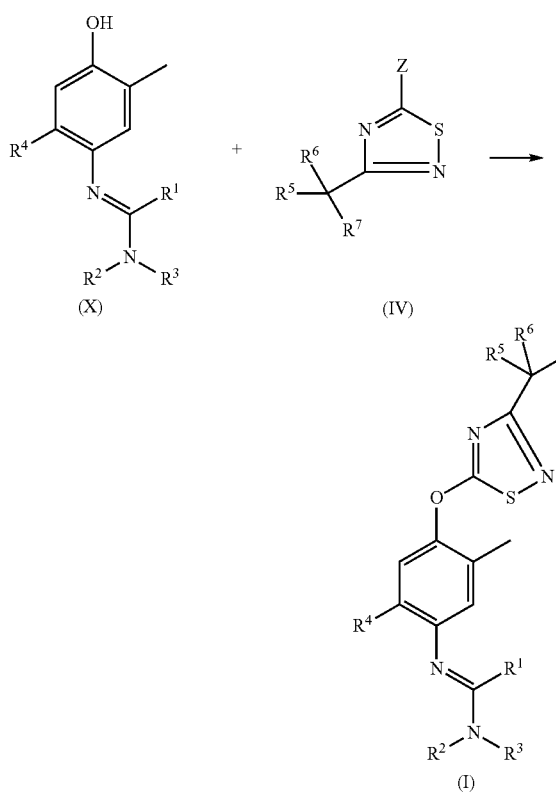

With regard to the reaction conditions, solvents and catalysts, reference may be made to stage (f) and to Tables I and II.

In connection with the processes according to the invention for the preparation of the amidines of the formula (I), the following combinations of reaction stages are to be regarded as advantageous: stages (a), (e) and (f); stages (b), (e) and (f); stages (c) and (f); stages (d) and (f); stages (h) and (i) and/or stages (g) and (j).

The preparation of the thiadiazolyloxyphenylamidines according to the invention takes place, if appropriate, without intermediate isolation of the intermediates.

The concluding purifying of the thiadiazolyloxyphenylamidines can, if appropriate, take place by normal purification methods. Preferably, purification is carried out by crystallization.

The thiadiazolyl derivatives of the formula (IVa) in which Z is a chlorine atom used in stages (b), (d) and (j) of the process described above can, for example, be obtained in accordance with the process described in the following scheme or the processes described in DE-A-960281 or in Chemische Berichte, 90, 182-7, 1957:

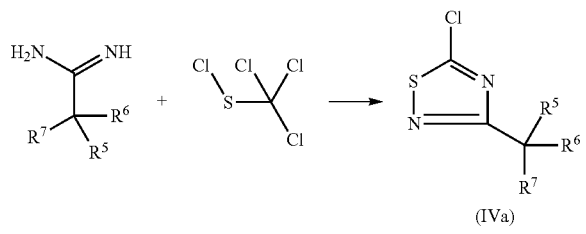

The chlorides of the formula (IVa) can be converted by acid hydrolysis into the alcohols of the formula (II).

The thiadiazolyl derivatives of the formula (IVb) in which Z is a tosyl group used in stages (b), (d) and (j) of the process described above can, for example, be obtained in accordance with the process described in the following scheme:

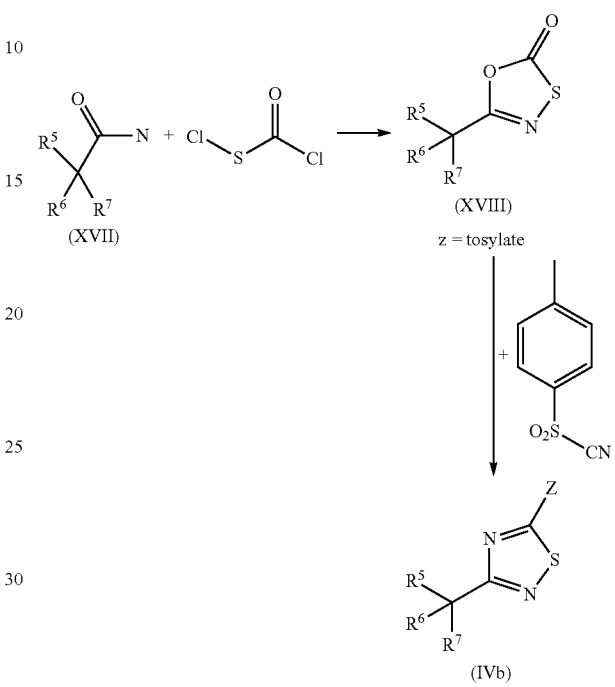

The carboxamides of the general formula (XVII) used can, for example, be prepared according to the instructions in Houben-Weyl, VIII, p. 655ff.

Combating of Undesirable Microorganisms

The amidines according to the invention exhibit a strong microbicidal action and can be used for combating undesirable microorganisms, such as fungi and bacteria, in plant protection and in material protection.

Plant Protection

Fungicides can be used in plant protection for combating Plasmodiophoromycetes, Oomycetes, Chytridiomycetes, Zygomycetes, Ascomycetes, Basidiomycetes and Deuteromycetes.

Bactericides can be used in plant protection for combating Pseudomonadaceae, Rhizobiaceae, Enterobacteriaceae, Corynebacteriaceae and Streptomycetaceae.

Mention may be made, by way of example but without limitation, of some pathogens of fungal and bacterial diseases which come under the generic terms listed above:

diseases caused by pathogens of powdery mildew, such as, for example,

Blumeria species, such as, for example, Blumeria graminis;

Podosphaera species, such as, for example, Podosphaera leucotricha;

Sphaerotheca species, such as, for example, Sphaerotheca fuliginea;

Uncinula species, such as, for example, Uncinula necator;

diseases caused by rust pathogens, such as, e.g.,

Gymnosporangium species, such as, for example, Gymnosporangium sabinae;

Hemileia species, such as, for example, *Hemileia vastatrix*;
Phakopsora species, such as, for example, *Phakopsora pachyrhizi* and *Phakopsora meibomiae*;
Puccinia species, such as, for example, *Puccinia recondita*;
Uromyces species, such as, for example, *Uromyces appendiculatus*;
diseases caused by pathogens of the Oomycetes group, such as, e.g.,
Bremia species, such as, for example, *Bremia lactucae*;
Peronospora species, such as, for example, *Peronospora pisi* or *P. brassicae*;
Phytophthora species, such as, for example, *Phytophthora infestans*;
Plasmopara species, such as, for example, *Plasmopara viticola*;
Pseudoperonospora species, such as, for example, *Pseudoperonospora humuli* or *Pseudoperonospora cubensis*;
Pythium species, such as, for example, *Pythium ultimum*;
leaf spot diseases and leaf wilts caused by, e.g.,
Alternaria species, such as, for example, *Alternaria solani*;
Cercospora species, such as, for example, *Cercospora beticola*;
Cladosporium species, such as, for example, *Cladosporium cucumerinum*;
Cochliobolus species, such as, for example, *Cochliobolus sativus* (conidial form: *Drechslera*, syn: *Helminthosporium*);
Colletotrichum species, such as, for example, *Colletotrichum lindemuthanium*;
Cycloconium species, such as, for example, *Cycloconium oleaginum*;
Diaporthe species, such as, for example, *Diaporthe citri*;
Elsinoe species, such as, for example, *Elsinoe fawcettii*;
Gloeosporium species, such as, for example, *Gloeosporium laeticolor*;
Glomerella species, such as, for example, *Glomerella cingulata*;
Guignardia species, such as, for example, *Guignardia bidwelli*;
Leptosphaeria species, such as, for example, *Leptosphaeria maculans*;
Magnaporthe species, such as, for example, *Magnaporthe grisea*;
Mycosphaerella species, such as, for example, *Mycosphaerella graminicola* and *Mycosphaerella fijiensis*;
Phaeosphaeria species, such as, for example, *Phaeosphaeria nodorum*;
Pyrenophora species, such as, for example, *Pyrenophora teres*;
Ramularia species, such as, for example, *Ramularia collo-cygni*;
Rhynchosporium species, such as, for example, *Rhynchosporium secalis*;
Septoria species, such as, for example, *Septoria apii*;
Typhula species, such as, for example, *Typhula incarnata*;
Venturia species, such as, for example, *Venturia inaequalis*;
root and stalk diseases caused by, e.g.,
Corticium species, such as, for example, *Corticium graminearum*;
Fusarium species, such as, for example, *Fusarium oxysporum*;
Gaeumannomyces species, such as, for example, *Gaeumannomyces graminis*;
Rhizoctonia species, such as, for example, *Rhizoctonia solani*;
Tapesia species, such as, for example, *Tapesia acuformis*;
Thielaviopsis species, such as, for example, *Thielaviopsis basicola*;
ear and panicle diseases (including maize cobs) caused by, e.g.,
Alternaria species, such as, for example, *Alternaria* spp.;
Aspergillus species, such as, for example, *Aspergillus flavus*;
Cladosporium species, such as, for example, *Cladosporium cladosporioides*;
Claviceps species, such as, for example, *Claviceps purpurea*;
Fusarium species, such as, for example, *Fusarium culmorum*;
Gibberella species, such as, for example, *Gibberella zeae*;
Monographella species, such as, for example, *Monographella nivalis*;
diseases caused by smuts, such as, e.g.,
Sphacelotheca species, such as, for example, *Sphacelotheca reiliana*;
Tilletia species, such as, for example, *Tilletia caries*;
Urocystis species, such as, for example, *Urocystis occulta*;
Ustilago species, such as, for example, *Ustilago nuda*;
fruit rot caused by, e.g.,
Aspergillus species, such as, for example, *Aspergillus flavus*;
Botrytis species, such as, for example, *Botrytis cinerea*;
Penicillium species, such as, for example, *Penicillium expansum* and *Penicillium purpurogenum*;
Sclerotinia species, such as, for example, *Sclerotinia sclerotiorum*;
Verticilium species, such as, for example, *Verticilium alboatrum*;
seed- and soil-borne rots and wilts, and seedling diseases, caused by, e.g.,
Alternaria species, such as, for example, *Alternaria brassicicola*;
Aphanomyces species, such as, for example, *Aphanomyces euteiches*;
Ascochyta species, such as, for example, *Ascochyta lentis*;
Aspergillus species, such as, for example, *Aspergillus flavus*;
Cladosporium species, such as, for example, *Cladosporium herbarum*;
Cochliobolus species, such as, for example, *Cochliobolus sativus* (conidial form: *Drechslera*, *Bipolaris* syn: *Helminthosporium*);
Colletotrichum species, such as, for example, *Colletotrichum coccodes*;
Fusarium species, such as, for example, *Fusarium culmorum*;
Gibberella species, such as, for example, *Gibberella zeae*;
Macrophomina species, such as, for example, *Macrophomina phaseolina*;
Monographella species, such as, for example, *Monographella nivalis*;
Penicillium species, such as, for example, *Penicillium expansum*;
Phoma species, such as, for example, *Phoma lingam*;
Phomopsis species, such as, for example, *Phomopsis sojae*;
Phytophthora species, such as, for example, *Phytophthora cactorum*;
Pyrenophora species, such as, for example, *Pyrenophora graminea*;
Pyricularia species, such as, for example, *Pyricularia oryzae*;
Pythium species, such as, for example, *Pythium ultimum*;

*Rhizoctonia* species, such as, for example, *Rhizoctonia solani;*

*Rhizopus* species, such as, for example, *Rhizopus oryzae;*

*Sclerotium* species, such as, for example, *Sclerotium rolfsii;*

*Septoria* species, such as, for example, *Septoria nodorum;*

*Typhula* species, such as, for example, *Typhula incarnata;*

*Verticillium* species, such as, for example, *Verticillium dahliae;* cankers, galls and witches' broom disease caused by, e.g., *Nectria* species, such as, for example, *Nectria galligena;* wilts caused by, e.g.,

*Monilinia* species, such as, for example, *Monilinia laxa;* deformations of leaves, flowers and fruits caused by, e.g.,

*Taphrina* species, such as, for example, *Taphrina deformans;* degenerative diseases of woody plants caused by, e.g.,

*Esca* species, such as, for example, *Phaeomoniella chlamydospora, Phaeoacremonium aleophilum* and *Fomitiporia mediterranea;* flower and seed diseases caused by, e.g.,

*Botrytis* species, such as, for example, *Botrytis cinerea;* diseases of plant tubers caused by, e.g.,

*Rhizoctonia* species, such as, for example, *Rhizoctonia solani;*

*Helminthosporium* species, such as, for example, *Helminthosporium solani;* diseases caused by bacterial pathogens, such as, e.g.,

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora.*

Preferably, the following diseases of soybeans can be combated:

fungal diseases on leaves, stalks, pods and seeds caused by, e.g., alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

fungal diseases on roots and the stem base caused by, e.g., black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active substances according to the invention also exhibit a strong strengthening activity in plants. They are accordingly suitable for mobilizing intrinsic defences of plants against attack by undesirable microorganisms.

In the present context, plant-strengthening (resistance-inducing) substances are to be understood as meaning those materials which are capable of stimulating the defence system of plants such that the treated plants, on subsequent inoculation with undesirable microorganisms, exhibit extensive resistance to these microorganisms.

In the present case, undesirable microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active substances.

The fact that the active substances are well tolerated by plants in the concentrations necessary for combating plant diseases makes possible treatment of aboveground plant parts, of plant propagation material and seed, and of the soil.

In this connection, the active substances according to the invention can be used particularly successfully in combating cereal diseases, such as, e.g., *Puccinia* species, and diseases in viticulture and in the cultivation of fruit and vegetables, such as, e.g., *Botrytis, Venturia* or *Alternaria* species.

The active substances according to the invention are also suitable for increasing the crop yield. In addition, they are of lower toxicity and are well tolerated by plants.

The active substances according to the invention can also optionally be used, in specific concentrations and application amounts, as herbicides, for affecting plant growth and for combating animal pests. They can optionally also be used as intermediates and precursors for the synthesis of additional active substances.

All plants and plant parts can be treated according to the invention. In this connection, plants are to be understood as meaning all plants and plant populations, such as desirable and undesirable wild plants or cultivated plants (including naturally occurring cultivated plants). Cultivated plants can be plants which can be obtained by conventional breeding and optimization methods or by biotechnological and genetic engineering methods or combinations of these methods, including transgenic plants and including plant varieties which may or may not be protected by laws on variety certification. Plant parts should be understood as meaning all aboveground and subsoil parts and organs of plants, such as shoot, leaf, flower and root, examples which are listed being leaves, needles, stalks, stems, flowers, fruiting bodies, fruits and seeds, and also roots, tubers and rhizomes. Plant parts also include harvested crops, and also vegetative and generative propagation material, for example cuttings, tubers, rhizomes, layers and seeds.

The treatment according to the invention of the plants and plant parts with the active substances is carried out directly or by acting on the environment, habitat or storage area thereof using conventional treatment methods, e.g. by dipping, spraying, evaporating, atomizing, scattering, spreading and, with propagation material, in particular with seeds, furthermore by coating with one or more layers.

Mycotoxins

In addition, it is possible, by the treatment according to the invention, to reduce the mycotoxin content in harvested crops and the foodstuffs and feedstuffs prepared therefrom. In this connection, mention may in particular but not exclusively be made of the following mycotoxins: deoxynivalenol (DON), nivalenol, 15-Ac-DON, 3-Ac-DON, T2 and HT2 toxin, fumonisins, zearalenone, moniliformin, fusarin, diacetoxyscirpenol (DAS), beauvericin, enniatin, fusaroproliferin, fusarenol, ochratoxins, patulin, ergot alkaloids and aflatoxins, which can be caused, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, and others, and also by *Aspergillus* spec., *Penicillium* spec., *Claviceps purpurea, Stachybotrys* spec., and others.

Material Protection

In material protection, the substances according to the invention can be used for the protection of industrial materials from attack and destruction by undesirable microorganisms.

Industrial materials are to be understood in the present context as meaning nonliving materials which have been prepared for use in industry. For example, industrial materials which are to be protected by active substances according to the invention from microbial change or destruction can be adhesives, sizes, paper and board, textiles, leather, wood, paints and plastic articles, cooling lubricants and other materials which can be attacked or destroyed by microorganisms. In the context of the materials to be protected, mention may also be made of parts of production plants, for example cooling water circuits, which can be detrimentally affected by proliferation of microorganisms. In the context of the present invention, mention may preferably be made, as industrial materials, of adhesives, sizes, papers and boards, leather, wood, paints, cooling lubricants and heat-transfer liquids, particularly preferably of wood.

Examples which may be mentioned of microorganisms which can decompose or modify industrial materials are bacteria, fungi, yeasts, algae and slime organisms. The active substances according to the invention are preferably active against fungi, in particular moulds, wood-discolouring and wood-destroying fungi (Basidiomycetes), and against slime organisms and algae.

Mention may be made, by way of example, of microorganisms of the following genera:
  *Alternaria*, such as *Alternaria tenuis*,
  *Aspergillus*, such as *Aspergillus niger*,
  *Chaetomium*, such as *Chaetomium globosum*,
  *Coniophora*, such as *Coniophora puetana*,
  *Lentinus*, such as *Lentinus tigrinus*,
  *Penicillium*, such as *Penicillium glaucum*,
  *Polyporus*, such as *Polyporus versicolor*,
  *Aureobasidium*, such as *Aureobasidium pullulans*,
  *Sclerophoma*, such as *Sclerophoma pityophila*,
  *Trichoderma*, such as *Trichoderma viride*,
  *Escherichia*, such as *Escherichia coli*,
  *Pseudomonas*, such as *Pseudomonas aeruginosa*,
  *Staphylococcus*, such as *Staphylococcus aureus*.

Formulations

The present invention relates to a composition for combating undesirable microorganisms, comprising at least one of the thiadiazolyloxyphenylamidines according to the invention.

The thiadiazolyloxyphenylamidines according to the invention can for this, depending on their respective physical and/or chemical properties, be converted into the standard formulations, such as solutions, emulsions, suspensions, powders, foams, pastes, granules, aerosols, very fine encapsulations in polymeric substances and in coating materials for seed, and also ULV cold- and hot-fogging formulations.

These formulations are prepared in a known way, e.g. by mixing the active substances with extenders, that is liquid solvents, liquefied gases under pressure and/or solid carriers, optionally with the use of surface-active agents, that is emulsifiers and/or dispersants and/or foaming agents. In the case of the use of water as extender, use may also be made, e.g., of organic solvents as cosolvents. Possible liquid solvents are essentially: aromatic hydrocarbons, such as xylene, toluene or alkylnaphthalenes, chlorinated aromatic hydrocarbons or chlorinated aliphatic hydrocarbons, such as chlorobenzenes, chloroethylenes or methylene chloride, aliphatic hydrocarbons, such as cyclohexane or paraffins, e.g. petroleum fractions, alcohols, such as butanol or glycol, and the ethers and esters thereof, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are to be understood as meaning those liquids which are in the gas form at standard temperature and at standard pressure, e.g. aerosol propellants, such as halogenated hydrocarbons and also butane, propane, nitrogen and carbon dioxide. Possible solid carriers are, e.g., ground natural minerals, such as kaolins, argillaceous earths, talc, chalk, quartz, attapulgite, montmorillonite or diatomaceous earth, and ground synthetic minerals, such as highly dispersed silica, aluminium oxide and silicates. Possible solid carriers for granules are, e.g., broken and fractionated natural rocks, such as calcite, pumice, marble, sepiolite or dolomite, and also synthetic granules formed from inorganic and organic dusts, and also granules formed from organic material, such as sawdust, coconut shells, maize cobs and tobacco stalks. Possible emulsifiers and/or foaming agents are, e.g., nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates, and also protein hydrolysates. Possible dispersants are, e.g., lignosulphite waste liquors and methylcellulose.

Use may be made, in the formulations, of stickers, such as carboxymethylcellulose, natural and synthetic polymers in the powder, granule or latex form, such as gum arabic, polyvinyl alcohol, polyvinyl acetate, and also natural phospholipids, such as cephalins and lecithins, and synthetic phospholipids. Other possible additives are mineral and vegetable oils.

Use may also be made of colorants, such as inorganic pigments, e.g. iron oxide, titanium oxide, Prussian blue, and organic colorants, such as alizarin dyes, azo dyes and metal phthalocyanine dyes, and trace elements, such as salts of iron, manganese, boron, copper, cobalt, molybdenum and zinc.

The formulations generally comprise between 0.1 and 95% by weight of active substance, preferably between 0.5 and 90%.

The formulations described above can be used in a method according to the invention for combating undesirable microorganisms, in which the thiadiazolyloxyphenylamidines according to the invention are applied to the microorganisms and/or to the habitat thereof.

Seed Treatment

The combating of phytopathogenic fungi by the treatment of the seed of plants has been known for a long time and is the subject-matter of continuous improvements. Nevertheless, a series of problems arises in the treatment of seed, which problems may not always be satisfactorily solved. Thus, it is desirable to develop methods for protecting the seed and the germinating plant which render superfluous or at least markedly reduce the additional application of plant protection compositions after sowing or after emergence of the plants. It is furthermore desirable to optimize the amount of the active substance used, so that the seed and the germinating plant are given the best possible protection against attack by phytopathogenic fungi but without the plant itself being damaged by the active substance used. In particular, methods for the treatment of seed should also include the intrinsic fungicidal properties of transgenic plants in order to achieve optimum protection of the seed and the germinating plant with a minimum expenditure of plant protection compositions.

The present invention therefore also relates in particular to a method for the protection of seed and germinating plants from attack by phytopathogenic fungi, by treating the seed with a composition according to the invention.

The invention likewise relates to the use of the compositions according to the invention for the treatment of seed to protect the seed and the germinating plant from phytopathogenic fungi.

Furthermore, the invention relates to seed which has been treated with a composition according to the invention in order to protect from phytopathogenic fungi.

One of the advantages of the present invention is that, because of the particular systemic properties of the compositions according to the invention, the treatment of the seed with these compositions not only protects the seed itself from phytopathogenic fungi but also protects the plants resulting therefrom after emergence from phytopathogenic fungi. In this way, the immediate treatment of the crop at the time of sowing or shortly thereafter can be dispensed with.

It is likewise to be regarded as advantageous that the mixtures according to the invention can in particular also be used with transgenic seed.

The compositions according to the invention are suitable for the protection of seed of any plant variety used in agriculture, in the greenhouse, in forests or in horticulture. The seed concerned in this connection is in particular seed of cereals (such as wheat, barley, rye, millet and oats), maize, cotton, soya, rice, potatoes, sunflowers, beans, coffee, beet (e.g., sugarbeet and forage beet), peanuts, vegetables (such as tomatoes, cucumbers, onions and lettuce), lawns and ornamental plants. The treatment of the seed of cereals (such as wheat, barley, rye and oats), maize and rice is of particular importance.

In the context of the present invention, the composition according to the invention is applied to the seed alone or in a suitable formulation. Preferably, the seed is treated in a condition sufficiently stable for no damage to occur during the treatment. In general, the treatment of the seed can be carried out at any point in time between harvesting and sowing. Use is usually made of seed which has been separated from the plant and freed from pods, shells, stalks, skins, hairs or fruit flesh. Thus, it is possible, for example, to use seed which has been harvested, cleaned and dried up to a moisture content of less than 15% by weight. Alternatively, it is also possible to use seed which, after drying, has been treated, e.g. with water, and then dried again.

In general, care must be taken, in the treatment of the seed, that the amount of the composition according to the invention and/or of additional additives applied to the seed is chosen so that the germination of the seed is not impaired or that the plant resulting therefrom is not damaged. This is to be taken into consideration in particular with active substances which may show phytotoxic effects at certain application rates.

The compositions according to the invention can be applied immediately, thus without comprising additional components and without having been diluted. It is generally preferable to apply the compositions to the seed in the form of a suitable formulation. Suitable formulations and methods for seed treatment are known to a person skilled in the art and are described, e.g., in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active substance combinations which can be used according to the invention can be converted into the usual seed dressing formulations, such as solutions, emulsions, suspensions, powders, foams, slurries or other coating materials for seed, and also ULV formulations.

These formulations are prepared in a known way by mixing the active substances or active substance combinations with conventional additives, such as, for example, conventional extenders and also solvents or diluents, colorants, wetting agents, dispersants, emulsifiers, antifoaming agents, preservatives, secondary thickeners, adhesives, gibberellins and also water.

Suitable colorants which may be present in the seed dressing formulations which can be used according to the invention comprise all colorants conventional for such purposes. In this connection, use may be made both of pigments, which are sparingly soluble in water, and dyes, which are soluble in water. Mention may be made, as examples, of the colorants known under the descriptions Rhodamine B, C.I. Pigment Red 112 and C.I. Solvent Red 1.

Possible wetting agents which can be present in the seed dressing formulations which can be used according to the invention comprise all substances which promote wetting and are conventional in the formulation of agrochemical active substances. Use may preferably be made of alkylnaphthalenesulphonates, such as diisopropyl- or diisobutylnaphthalenesulphonates.

Suitable dispersants and/or emulsifiers which may be present in the seed dressing formulations which can be used according to the invention comprise all nonionic, anionic and cationic dispersants conventional in the formulation of agrochemical active substances. Use may preferably be made of nonionic or anionic dispersants or mixtures of nonionic or anionic dispersants. Mention may in particular be made, as suitable nonionic dispersants, of ethylene oxide/propylene oxide block polymers, alkylphenol polyglycol ethers and also tristyrylphenol polyglycol ethers, and the phosphated or sulphated derivatives thereof Suitable anionic dispersants are in particular lignosulphonates, polyacrylic acid salts and arylsulphonate/formaldehyde condensates.

Antifoaming agents which may be present in the seed dressing formulations which can be used according to the invention comprise all foam-inhibiting substances conventional in the formulation of agrochemical active substances. Use may preferably be made of silicone defoaming agents and magnesium stearate.

Preservatives which may be present in the seed dressing formulations which can be used according to the invention comprise all substances which can be used in agrochemical compositions for such purposes. Mention may be made, by way of example, of dichlorophen and benzyl alcohol hemiformal.

Possible secondary thickeners which may be present in the seed dressing formulations which can be used according to the invention comprise all substances which can be used in agrochemical compositions for such purposes. Preferably suitable are cellulose derivatives, acrylic acid derivatives, xanthan, modified clays and highly dispersed silica.

Possible adhesives which may be present in the seed dressing formulations which can be used according to the invention comprise all conventional binders which can be used in seed dressings. Mention may preferably be made of polyvinylpyrrolidone, polyvinyl acetate, polyvinyl alcohol and tylose.

Possible gibberellins which may be present in the seed dressing formulations which can be used according to the invention preferably comprise gibberellins A1, A3 (=gibberellic acid), A4 and A7; use is particularly preferably made of gibberellic acid. Gibberellins are known (cf. R. Wegler, "Chemie der Pflanzenschutz- and Schädlingsbekämpfungsmittel" [Chemistry of Plant Protection and Pest Control Agents], Vol. 2, Springer Verlag, 1970, pp. 401-412).

The seed dressing formulations which can be used according to the invention can be used, either directly or after prior diluting with water, for the treatment of seed of the most varied species. Thus, the concentrates or the compositions which can be obtained therefrom by diluting with water can be used for the dressing of the seed of cereals, such as wheat, barley, rye, oats and triticale, and also the seed of maize, rice, rape, peas, beans, cotton, sunflowers and beet, or also of vegetable seed of the most varied natures. The seed dressing formulations which can be used according to the invention or the diluted compositions thereof can also be used for the dressing of seed of transgenic plants. In this connection, additional synergistic effects may also occur in interaction with the substances formed by expression.

All mixing devices which can be conventionally used for dressing are suitable for the treatment of seed with the seed dressing formulations which can be used according to the invention or the compositions prepared therefrom by addition of water. Specifically, the dressing procedure is such that the seed is introduced into a mixer, the amount of seed dressing formulation desired each time is added, either as such or after prior dilution with water, and mixing is carried out until the formulation is uniformly distributed over the seed. If appropriate, a drying operation follows.

The application rate of the seed dressing formulations which can be used according to the invention can be varied within a relatively wide range. It depends on the respective content of the active substances in the formulations and on the seed. The application rates of active substance combination are generally between 0.001 and 50 g per kilogram of seed, preferably between 0.01 and 15 g per kilogram of seed.

Mixture with Known Fungicides, Bactericides, Acaricides, Nematicides or Insecticides The amidines according to the invention can be used, as such or in their formulations, also in a mixture with known fungicides, bactericides, acaricides, nematicides or insecticides, in order thus, e.g., to broaden the spectrum of activity or to prevent the development of resistance.

A mixture with other known active substances, such as herbicides, or with fertilizers and growth regulators, safeners or semiochemicals is also possible.

In addition, the compounds of the formula (I) according to the invention also exhibit very good antimycotic activities. They have a very broad spectrum of antimycotic activity, in particular against dermatophytes and budding fungi, moulds and diphasic fungi (e.g. against *Candida* species, such as *Candida albicans, Candida glabrata*), and also *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The enumeration of these fungi does not represent in any way a limitation on the mycotic spectrum which can be included but has only an illustrative nature.

The thiadiazolyloxyphenylamidines according to the invention can accordingly be used both in medicinal and in nonmedicinal applications.

The active substances can be applied as such, in the form of their formulations or in the form of the application forms prepared therefrom, such as ready-to-use solutions, suspensions, wettable powders, pastes, soluble powders, dusts and granules. Application takes place in standard fashion, e.g. by pouring, spraying, atomizing, scattering, dusting, foaming, spreading, and the like. It is furthermore possible to apply the active substances by the ultra-low-volume method or to inject the active substance composition or the active substance itself into the soil.

The seed of the plant can also be treated.

When the thiadiazolyloxyphenylamidines according to the invention are used as fungicides, the application rates can be varied within a relatively wide range depending on the type of application. In the treatment of plant parts, the application rates of active substance are generally between 0.1 and 10 000 g/ha, preferably between 10 and 1000 g/ha. In seed treatment, the application rates of active substance are generally between 0.001 and 50 g per kilogram of seed, preferably between 0.01 and 10 g per kilogram of seed. In soil treatment, the application rates of active substance are generally between 0.1 and 10 000 g/ha, preferably between 1 and 5000 g/ha.

GMOs

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference-RNAi technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active substances and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active substance combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active substances.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. the said plants show a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in the said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pot dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or hybrid vigour which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) have for instance been described in *Brassica* species. However, genetic determinants for male sterility can also be located in the nuclear genome. Male sterile plants can also be obtained by plant biotechnology methods, such as genetic engineering. A particularly useful means of obtaining male-sterile plants is described in WO 89/10396 in which, for example, a ribonuclease, such as barnase, is selectively expressed in the tapetum cells in the stamens. Fertility can then be restored by expression in the tapetum cells of a ribonuclease inhibitor, such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS or an eleusine EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the abovementioned genes.

Other herbicide-resistant plants are for example plants that are made tolerant to herbicides inhibiting the enzyme glutamine synthase, such as bialaphos, phosphinotricin or glufosinate. Such plants can be obtained by expressing an enzyme detoxifying the herbicide or a mutant of the glutamine synthase enzyme that is resistant to inhibition. One such efficient detoxifying enzyme is an enzyme encoding a phosphinotricin acetyltransferase (such as the bar or pat protein from *Streptomyces* species). Plants expressing an exogenous phosphinotricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme.

Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants is described in international publication WO 1996/033270. Further sulphonylurea- and imidazolinone-tolerant plants are also described in, for example, WO 2007/024782.

Other plants tolerant to imidazolinone and/or sulphonylurea can be obtained by induced mutagenesis, selection in cell cultures in the presence of herbicide or mutation breeding.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from Bacillus thuringiensis or an insecticidal portion thereof, such as the insecticidal crystal proteins described online at: http://www.lifesci.sussex.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal (VIP) proteins listed at http://www.lifesci.sussex.ac.uk/Home/Neil_Crickmore/Bt/vip.html, e.g., proteins from VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
a. plants which contain a transgene capable of reducing the expression and/or the activity of the poly(ADP-ribose) polymerase (PARP) gene in the plant cells or plants;
b. plants which contain a stress tolerance enhancing transgene capable of reducing the expression and/or activity of the PARG encoding genes of the plants or plant cells;
c. plants which contain a stress tolerance enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.

2) transgenic plants which synthesize nonstarch carbohydrate polymers or which synthesize nonstarch carbohydrate polymers with altered properties in comparison to wild type plants without genetic modification. Examples are plants producing polyfructose, especially of the inulin and levan type, plants producing alpha-1,4-glucans, plants producing alpha-1,6 branched alpha-1,4-glucans and plants producing alternan.

3) transgenic plants which produce hyaluronan.

Plants or plant cultivars (obtained by plant biotechnology methods, such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
- a) plants, such as cotton plants, containing an altered form of cellulose synthase genes,
- b) plants, such as cotton plants, containing an altered form of rsw2 or rsw3 homologous nucleic acids;
- c) plants, such as cotton plants, with increased expression of sucrose phosphate synthase;
- d) plants, such as cotton plants, with increased expression of sucrose synthase;
- e) plants, such as cotton plants, wherein the timing of the plasmodesmatal gating at the basis of the fibre cell is altered, e.g. through downregulation of fibre selective β-1,3-glucanase;
- f) plants, such as cotton plants, having fibres with altered reactivity, e.g. through the expression of N-acetylglucosamine transferase gene including nodC and chitin synthase genes.

Plants or plant cultivars (obtained by plant biotechnology methods, such as genetic engineering) which may also be treated according to the invention are plants, such as oilseed rape or related Brassica plants, with altered oil profile characteristics. Such plants can be obtained by genetic transformation or by selection of plants containing a mutation imparting such altered oil characteristics and include:
- a) plants, such as oilseed rape plants, producing oil having a high oleic acid content;
- b) plants such as oilseed rape plants, producing oil having a low linolenic acid content;
- c) plants such as oilseed rape plants, producing oil having a low level of saturated fatty acids.

Particularly useful transgenic plants which may be treated according to the invention are plants which comprise one or more genes which encode one or more toxins are the transgenic plants which are sold under the following trade names: YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soybean varieties which are sold under the following trade names: Roundup Ready® (tolerance to glyphosate, for example maize, cotton, soybean), Liberty Link® (tolerance to phosphinotricin, for example oilseed rape), IMI® (tolerance to imidazolinone) and SCS® (tolerance to sulphonylurea), for example maize. Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

PREPARATION EXAMPLES

| No. | $R^1$ | $R^2$ | $R^3$ | $R^4$ | $R^5$ | $R^6$ | $R^7$ |
|---|---|---|---|---|---|---|---|
| 1 | H | Ethyl | $CH_3$ | Chloro | $CH_3$ | $CH_3$ | $CH_3$ |
| 2 | H | Ethyl | $CH_3$ | Bromo | $CH_3$ | $CH_3$ | $CH_3$ |
| 3 | H | Ethyl | $CH_3$ | Chloro | | | 1-Chlorocyclopropyl |
| 4 | H | Propan-2-yl | $CH_3$ | Chloro | | | 1-Chlorocyclopropyl |
| 5 | H | —$(CH_2)_5$— | | Chloro | | | 1-Chlorocyclopropyl |
| 6 | H | Ethyl | $CH_3$ | Chloro | $CH_3$ | H | 4-Chlorophenyl |
| 7 | H | —$(CH_2)_5$— | | Chloro | $CH_3$ | H | 4-Chlorophenyl |
| 8 | H | Propan-2-yl | $CH_3$ | Chloro | $CH_3$ | H | 4-Chlorophenyl |
| 9 | H | Ethyl | $CH_3$ | Chloro | H | H | 4-Chlorobenzyl |
| 10 | H | —$(CH_2)_5$— | | Chloro | H | H | 4-Chlorobenzyl |
| 11 | H | Ethyl | $CH_3$ | Chloro | $CH_3$ | $CH_3$ | 4-Chlorophenyl |
| 12 | H | —$(CH_2)_5$— | | Chloro | $CH_3$ | $CH_3$ | 4-Chlorophenyl |
| 13 | H | Propan-2-yl | $CH_3$ | Chloro | $CH_3$ | $CH_3$ | 4-Chlorophenyl |
| 14 | H | Ethyl | $CH_3$ | Chloro | H | H | Phenyl |
| 15 | H | Ethyl | $CH_3$ | Chloro | | | (E)-2-(4-Fluorophenyl)ethenyl |
| 16 | H | —$(CH_2)_5$— | | Chloro | | | (E)-2-(4-Fluorophenyl)ethenyl |
| 17 | H | Ethyl | $CH_3$ | Chloro | | | 1-(4-Chlorophenyl)cyclopropyl |
| 18 | H | Ethyl | $CH_3$ | Chloro | H | H | 4-Chlorophenyl |
| 19 | H | Ethyl | $CH_3$ | Chloro | H | H | Chloro |
| 20 | H | Propan-2-yl | $CH_3$ | Chloro | | | 1-(4-Chlorophenyl)cyclopropyl |
| 21 | H | —$(CH_2)_5$— | | Chloro | | | 1-(4-Chlorophenyl)cyclopropyl |
| 22 | H | Ethyl | $CH_3$ | Chloro | H | H | 4-Chlorophenoxy |
| 23 | H | Propan-2-yl | $CH_3$ | Chloro | | | (E)-2-(4-Fluorophenyl)ethenyl |
| 24 | H | Propyl | $CH_3$ | Chloro | $CH_3$ | $CH_3$ | $CH_3$ |
| 25 | H | Prop-2-en-1-yl | $CH_3$ | Chloro | $CH_3$ | $CH_3$ | $CH_3$ |
| 26 | H | Cyclopropylmethyl | $CH_3$ | Chloro | $CH_3$ | $CH_3$ | $CH_3$ |
| 27 | H | 3-Methoxypropyl | $CH_3$ | Chloro | $CH_3$ | $CH_3$ | $CH_3$ |
| 28 | H | Ethyl | $CH_3$ | Chloro | $CH_3$ | $CH_3$ | Benzyl |
| 29 | H | Ethyl | $CH_3$ | Chloro | | | (1S,2S)-2-Phenylcyclopropyl |
| 30 | H | —$(CH_2)_5$— | | Chloro | | | (1S,2S)-2-Phenylcyclopropyl |
| 31 | H | Propan-2-yl | $CH_3$ | Chloro | | | (1S,2S)-2-Phenylcyclopropyl |
| 32 | H | Ethyl | $CH_3$ | Chloro | | | 2,2-Dichloro-1-methylcyclopropyl |
| 33 | H | Ethyl | $CH_3$ | Chloro | H | H | 4-Bromophenyl |

-continued

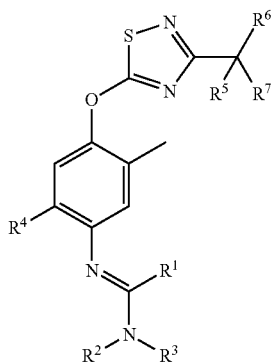

| No. | R¹ | R² | R³ | R⁴ | R⁵ | R⁶ | R⁷ |
|---|---|---|---|---|---|---|---|
| 34 | H | Ethyl | CH₃ | Chloro | H | H | 3-(Trifluoromethyl)phenyl |
| 35 | H | Ethyl | CH₃ | Chloro | H | H | 3-Chlorophenoxy |
| 36 | H | Ethyl | CH₃ | Chloro | H | H | 2-Chlorophenoxy |
| 37 | H | Ethyl | CH₃ | Chloro | H | H | Phenoxy |
| 38 | H | Ethyl | CH₃ | Chloro | H | H | 2,4-Dichlorophenyl |
| 39 | H | Ethyl | CH₃ | Chloro | CH₃ | CH₃ | Chloromethyl |
| 40 | H | Ethyl | CH₃ | Chloro | H | H | 2,4-Difluorophenyl |
| 41 | H | —(CH₂)₅— | | Chloro | H | H | Phenyl |
| 42 | H | Ethyl | CH₃ | Chloro | H | H | 4-[(Trifluoromethyl)sulphanyl]phenyl |

-continued

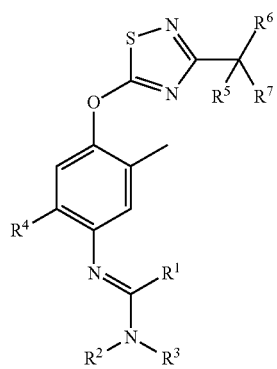

| No. | R¹ | R² | R³ | R⁴ | R⁵ | R⁶ | R⁷ |
|---|---|---|---|---|---|---|---|
| 43 | H | Ethyl | CH₃ | Chloro | | | 1,2,3,4-Tetrahydronaphth-2-yl |
| 44 | H | Propan-2-yl | CH₃ | Chloro | | | 1,2,3,4-Tetrahydronaphth-2-yl |
| 45 | H | —(CH₂)₅— | | Chloro | | | 1,2,3,4-Tetrahydronaphth-2-yl |
| 46 | H | Ethyl | CH₃ | Chloro | | | Phenyl |
| 47 | H | Ethyl | CH₃ | Chloro | | | 3,4-Difluorophenyl |
| 48 | H | Ethyl | CH₃ | Chloro | | | 3-(Trifluoromethoxy)phenyl |

| Ex. No. | ¹H NMR |
|---|---|
| 1 | 7.72(b, 1H); 7.45(s, 1H); 6.98(s, 1H); 3.44(q, 2H); 3.02(s, 3H); 2.12(s, 3H); 1.31(s, 9H); 1.16(t, 3H) |
| 2 | 7.71(b, 1H); 7.60(s, 1H); 6.98(s, 1H); 3.30(q, 2H); 2.98(s, 3H); 2.12(s, 3H); 1.31(s, 9H); 1.17(t, 3H) |
| 3 | 7.74(s, 1H); 7.47(s, 1H); 6.99(s, 1H); 3.46(m, 2H); 2.98(s, 3H); 2.14(s, 3H); 1.62(m, 2H); 1.52(m, 2H); 1.16(t, 3H) |
| 4* | 7.71(s, 1H); 7.32(s, 1H); 6.91(s, 1H); 3.76(sp, 1H); 2.91(s, 3H); 2.16(s, 3H); 1.65(m, 2H); 1.50(m, 2H); 1.24(d, 6H) |
| 5* | 7.58(s, 1H); 7.33(s, 1H); 6.92(s, 1H); 3.62(m, 2H); 3.34(m, 2H); 2.16(s, 3H); 1.66(m, 6H); 1.64(m, 2H); 1.50(m, 2H) |
| 6 | 7.73(s, 1H); 7.43(s, 1H); 7.30-7.37(m, 4H); 6.97(s, 1H); 4.31(q, 1H); 3.40(m, 2H); 2.97(s, 3H); 2.10(s, 3H); 1.58(d, 3H); 1.15(t, 3H) |
| 7 | 7.71(s, 1H); 7.44(s, 1H); 7.30-7.36(m, 4H); 6.98(s, 1H); 4.31(q, 1H); 3.48(m, 4H); 2.10(s, 3H); 1.52-1.67(m + d, 9H) |
| 8 | 7.78(s, 1H); 7.43(s, 1H); 7.30-7.36(m, 4H); 6.97(s, 1H); 4.31(q, 1H); 3.85(m, 1H); 2.88(s, 3H); 2.10(s, 3H); 1.58(d, 3H); 1.20(d, 6H) |
| 9 | 7.73(s, 1H); 7.42(s, 1H); 7.21-7.30(m, 4H); 6.98(s, 1H); 3.44(m, 2H); 2.91-3.17(m, 7H); 2.11(s, 3H); 1.16(t, 3H) |
| 10 | 7.71(s, 1H); 7.42(s, 1H); 7.21-7.32(m, 4H); 6.99(s, 1H); 3.49(m, 4H); 3.02-3.17(m, 4H); 2.11(s, 3H); 1.53-1.68(m, 6H) |
| 11 | 7.73(s, 1H); 7.43(s, 1H); 7.26-7.34(m, 4H); 6.97(s, 1H); 3.40(m, 2H); 2.97(s, 3H); 2.10(s, 3H); 1.69(s, 6H); 1.15(t, 3H) |
| 12 | 7.70(s, 1H); 7.43(s, 1H); 7.26-7.34(m, 4H); 6.98(s, 1H); 3.48(m, 4H); 2.10(s, 3H); 1.68(s, 6H); 1.51-1.66(m, 6H) |
| 13 | 7.78(s, 1H); 7.43(s, 1H); 7.25-7.35(m, 4H); 6.97(s, 1H); 3.85(m, 1H); 2.88(s, 3H); 2.10(s, 3H); 1.69(s, 6H); 1.20(d, 6H) |
| 14 | 7.73(s, 1H); 7.44(s, 1H); 7.29(m, 4H); 7.22(m, 1H); 6.97(s, 1H); 4.02(s, 2H); 3.39(m, 2H); 2.97(s, 3H); 2.11(s, 3H); 1.15(t, 3H) |
| 15 | 7.71-7.77(m + s, 3H); 7.60(d, 1H); 7.39(s, 1H); 7.18-7.23(m, 2H); 7.05-7.09(m, 2H); 3.41(m, 2H); 2.98(s, 3H); 2.21(s, 3H); 1.16(t, 3H) |
| 16 | 7.72-7.78(m + s, 3H); 7.60(d, 1H); 7.41(s, 1H); 7.18-7.23(m, 2H); 7.12(s, 1H); 7.07(d, 1H); 3.50(m, 4H); 2.21(s, 3H); 1.56-1.69(m, 6H) |
| 17 | 7.72(s, 1H); 7.44(s, 1H); 7.33-7.39(m, 4H); 6.97(s, 1H); 3.39(m, 2H); 2.97(s, 3H); 2.12(s, 3H); 1.56(m, 2H); 1.31(m, 2H); 1.15(t, 3H) |
| 18 | 7.72(s, 1H); 7.44(s, 1H); 7.30-7.36(m, 4H); 6.97(s, 1H); 4.09(s, 2H); 3.40(m, 2H); 2.97(s, 3H); 2.11(s, 3H); 1.15(t, 3H) |
| 19 | 7.74-1(b, 1H); 7.48(s, 1H); 7.00(s, 1H); 4.71(s, 2H); 2.98(s, 3H); 2.14(s, 3H); 1.16(t, 3H) |
| 20 | 7.78(s, 1H); 7.43(s, 1H); 7.33-7.41(m, 4H); 6.97(s, 1H); 3.85(m, 1H); 2.88(s, 3H); 2.12(s, 3H); 1.55(m, 2H); 1.31(m, 2H); 1.20(d, 6H) |
| 21 | 7.70(s, 1H); 7.43(s, 1H); 7.33-7.40(m, 4H); 6.98(s, 1H); 3.48(m, 4H); 2.12(s, 3H); 1.51-1.67(m, 8H); 1.31(m, 2H) |

| Ex. No. | $^1$H NMR |
|---|---|
| 22 | 7.73(b, 1H); 7.47(s, 1H); 7.31 + 7.03(AA'BB'; 4H); 6.99(s, 1H); 5.15(s, 2H); 2.98(s, 3H); 2.13(s, 3H); 1.16(t, 3H) |
| 23 | 7.70-7.82(m + s, 3H); 7.60(d, 1H); 7.50(s, 1H); 7.18-7.23(m, 2H); 7.07(s, 1H); 7.02(s, 1H); 3.85(m, 1H); 2.90(s, 3H); 2.17(s, 3H); 1.19(d, 6H) |
| 24 | 7.75(b, 1H); 7.46(s, 1H); 6.98(s, 1H); 3.39(t, 2H); 3.04(s, 3H); 2.13(s, 3H); 1.62(m, 2H); 1.27(s, 9H); 0.87(t, 3H) |
| 25 | 7.78(b, 1H); 7.46(s, 1H); 7.00(s, 1H); 5.87(m, 1H); 5.22(m, 2H); 3.98(m, 2H); 2.95(s, 3H); 2.14(s, 3H); 1.29(s, 9H) |
| 26 | 7.76(b, 1H); 7.46(s, 1H); 6.98(s, 1H); 3.32(d, 2H); 3.06(s, 3H); 2.13(s, 3H); 0.81(m, 1H); 0.50(m, 2H); 0.30(m, 2H) |
| 27 | 7.71(b, 1H); 7.46(s, 1H); 6.97(s, 1H); 3.34(m, 2H); 3.24(s, 3H); 2.12(s, 3H); 1.88(m, 2H); 1.62(m, 2H); 1.31(s, 9H) |
| 28 | 7.75(s, 1H); 7.45(s, 1H); 7.14-7.20(m, 3H); 7.01(s, 1H); 6.90(m, 1H); 3.42(m, 2H); 2.98(s, 2H); 2.95(s, 3H); 2.16(s, 3H); 1.29(s, 6H); 1.16(t, 3H) |
| 29 | 7.74(s, 1H); 7.46(s, 1H); 7.16-7.30(m, 5H); 6.99(s, 1H); 3.40(m, 2H); 2.97(s, 3H); 2.50(m, 1H); 2.40(m, 1H); 2.15(s, 3H); 1.62(m, 1H); 1.48(m, 1H); 1.16(t, 3H) |
| 30 | 7.71(s, 1H); 7.46(s, 1H); 7.16-7.29(m, 5H); 7.00(s, 1H); 3.48(m, 4H); 2.50(m, 1H); 2.39(m, 1H); 2.15(s, 3H); 1.46-1.68(m, 8H) |
| 31 | 7.79(s, 1H); 7.45(s, 1H); 7.16-7.30(m, 5H); 6.99(s, 1H); 3.85(m, 1H); 2.89(s, 3H); 2.50(m, 1H); 2.39(m, 1H); 2.15(s, 3H); 1.62(m, 1H); 1.48(m, 1H); 1.21(d, 6H) |
| 32 | 7.74(s, 1H); 7.46(s, 1H); 7.00(s, 1H); 3.40(m, 2H); 2.98(s, 3H); 2.48(d, 1H); 2.12(s, 3H); 1.86(d, 1H); 1.70(s, 3H); 1.16(t, 3H) |
| 33 | 7.73(s, 1H); 7.48(d, 2H); 7.44(s, 1H); 7.25(d, 2H); 6.98(s, 1H); 4.07(s, 2H); 3.40(m, 2H); 2.97(s, 3H); 2.11(s, 3H); 1.16(t, 3H) |
| 34 | 7.72(s, 1H); 7.65(s, 1H); 7.58(m, 3H); 7.44(s, 1H); 6.97(s, 1H); 4.22(s, 2H); 3.40(m, 2H); 2.97(s, 3H); 2.11(s, 3H); 1.16(t, 3H) |
| 35 | 7.73(b, 1H); 7.47(s, 1H); 7.32-6.97(m, 5H); 5.18(s, 2H); 2.98(s, 3H); 2.13(s, 3H); 1.16(t, 3H) |
| 36 | 7.73(b, 1H); 7.47(s, 1H); 7.42-6.96(m, 5H); 5.24(s, 2H); 2.98(s, 3H); 2.13(s, 3H); 1.16(t, 3H) |
| 37 | 7.73(b, 1H); 7.60-6.98(m, 6H); 5.13(s, 2H); 2.98(s, 3H); 2.13(s, 3H); 1.16(t, 3H) |
| 38 | 7.73(s, 1H); 7.56(d, 1H); 7.44(s, 1H); 7.40(d, 1H); 7.37(dd, 1H); 6.97(s, 1H); 4.21(s, 2H); 3.40(m, 2H); 2.97(s, 3H); 2.12(s, 3H); 1.16(t, 3H) |
| 39 | 7.74(s, 1H); 7.46(s, 1H); 6.99(s, 1H); 3.85(s, 2H); 3.41(m, 2H); 2.98(s, 3H); 2.13(s, 3H); 1.38(s, 6H); 1.16(t, 3H) |
| 40 | 7.72(s, 1H); 7.45(s, 1H); 7.41(m, 1H); 7.14(m, 1H); 7.02(m, 1H); 6.97(s, 1H); 4.10(s, 2H); 3.40(m, 2H); 2.97(t, 3H); 2.12(s, 3H); 1.15(t, 3H) |
| 41 | 7.73(s, 1H); 7.64(d, 2H); 7.45(d, 2H); 7.44(s, 1H); 6.98(s, 1H); 4.18(s, 2H); 3.40(m, 2H); 2.97(s, 3H); 2.11(s, 3H); 1.16(t, 3H) |
| 42 | 7.70(s, 1H); 7.44(s, 1H); 7.29(m, 4H); 7.22(m, 1H); 6.98(s, 1H); 4.08(s, 2H); 3.50(m, 4H); 2.11(s, 3H); 1.64(m, 2H); 1.54(m, 4H) |
| 43 | 7.74(bs, 1H); 7.45(s, 1H); 7.07-7.16(m, 4H); 6.98(s, 1H); 3.41(m, 2H); 3.00-3.22 (m, 3H); 2.97(s, 3H); 2.84(m, 2H); 2.24(m, 1H); 2.14(s, 3H); 1.90(m, 1H); 1.15(t, 3H) |
| 44 | 7.79(bs, 1H); 7.45(s, 1H); 7.07-7.12(m, 4H); 6.99(s, 1H); 3.80(m, 1H); 3.03-3.22 (m, 3H); 2.88(s, 3H); 2.84(m, 2H); 2.24(m, 1H); 2.14(s, 3H); 1.90(m, 1H); 1.20(d, 6H) |
| 45 | 7.71(s, 1H); 7.46(s, 1H); 7.07-7.11(m, 4H); 6.99(s, 1H); 3.48(m, 4H); 3.04-3.23 (m, 3H); 2.84(m, 2H); 2.24(m, 1H); 2.14(s, 3H); 1.90(m, 1H); 1.52-1.66(m, 6H) |

The chemical NMR shifts δ in ppm were measured at 400 MHz unless otherwise given in the solvent d$_6$-DMSO with tetramethylsilane as internal standard.
*Recording in the solvent CD$_3$CN
The following abbreviations describe the signal splitting:
s = singlet, d = doublet, t = triplet, q = quartet, m = multiplet The following abbreviations describe the signal splitting:
s=singlet, d=doublet, t=triplet, q=quartet, m=multiplet Synthetic Examples Example 3

N'-(2-Chloro-4-{[3-(1-chlorocyclopropyl)-1,2,4-thiadiazol-5-yl]oxy}-5-methylphenyl)-N-ethyl-N-methylimidoformamide 0.63 g (1.86 mmol) of 2-chloro-4-{[3-(1-chlorocyclopropyl)-1,2,4-thiadiazol-5-yl]oxy}-5-methylaniline is dissolved in 5 ml of toluene and treated with 0.50 g (3.71 mmol) of N-ethyl-N-methylformamide dimethyl acetal. The reaction mixture is refluxed for 12 h, subsequently cooled, freed from solvent under vacuum and purified by column chromatography. 0.62 g of product is obtained (82.0% purity, 71.3% yield; log P (pH 2.3)=1.62).

Synthesis of the Starting Compounds:

2-Chloro-4-{[3-(1-chlorocyclopropyl)-1,2,4-thiadiazol-5-yl]oxy}-5-methylaniline 3.00 g (19.04 mmol) of 2-chloro-4-hydroxy-5-methylaniline are introduced into 50 ml of acetonitrile, treated at ambient temperature with 3.16 g (22.84 mmol) of potassium carbonate and stirred at ambient temperature for 30 min. Subsequently, 6.26 g (19.04 mmol) of 3-(1-chlorocyclopropyl)-5-[(4-methylphenyl)sulphonyl]-1,2,4-thiadiazole are added and the reaction mixture is stirred at 50° C. for 12 h. After cooling, the mixture is concentrated on a rotary evaporator, the residue is taken up in dichloromethane and the solution is extracted twice with water, dried over Na$_2$SO$_4$ and freed from solvent under vacuum. The residue is purified by column chromatography. 3.18 g of product are obtained (93.3% purity, 49.4% yield, log P (pH 2.3)=3.50).

3-(1-Chlorocyclopropyl)-5-{(4-methylphenyl)sulphonyl}-1,2,4-thiadiazole 66.2 g (372 mmol) of 5-(1-chlorocyclopropyl)-1,3,4-oxathiazol-2-one and 70.9 g (391 mmol) of tosyl cyanide are stirred in 125 ml of 1,2-dichlorobenzene at 160° C. for 1 h. Subsequently, the reaction mixture is cooled and treated with pentane, and the precipitate is filtered off and dried under vacuum. 100.0 g of product are obtained (99.9% purity, 85.2% yield, log P (pH 2.3)=3.67).

5-(3-Chlorobenzyl)-1,3,4-oxathiazol-2-one 89.1 g (680 mmol) of chlorocarbonylsulphenyl chloride and 71.3 g (400 mmol) of (1-chlorocyclopropyl)carboxamide are stirred in 150 ml of toluene at 80° C. for 3 h. Subsequently, the solvent is removed under vacuum, the residue is treated with petroleum ether and the precipitate is filtered off and dried under vacuum. 66.2 g of product are obtained (97.9% purity, 91.2% yield).

Example 10

2-Chloro-4-({3-[2-(4-chlorophenyl)ethyl]-1,2,4-thiadiazol-5-yl}oxy)-5-methyl-N-[(Z)-piperidin-1-ylmethylidene]aniline 0.30 g (0.79 mmol) of 2-chloro-4-({3-[2-(4-chlorophenyl)ethyl]-1,2,4-thiadiazol-5-yl}oxy)-5-methylaniline is dissolved in 3 ml of toluene and 0.75 ml of methanol and treated with 0.37 g (2.37 mmol) of 1-(dimethoxylmethyl)piperidine. The reaction mixture is refluxed for 18 h, subsequently cooled, freed from the solvent under vacuum and purified by column chromatography. 0.13 g of product is obtained (84.2% purity, 29.3% yield, log P (pH 2.3)=2.64).

Synthesis of the Starting Compounds:

2-Chloro-4-({3-[2-(4-chlorophenyl)ethyl]-1,2,4-thiadiazol-5-yl}oxy)-5-methylaniline 1.45 g (9.24 mmol) of 2-chloro-4-hydroxy-5-methylaniline are introduced into 18 ml of acetonitrile, treated with 1.53 g (11.08 mmol) of potassium carbonate at ambient temperature and stirred at ambient temperature for 30 min. Subsequently, 3.50 g (9.24 mmol) of 3-[2-(4-chlorophenyl)ethyl]-5-[(4-methylphenyl]sulphonyl]-1,2,4-thiadiazole are added and the reaction mixture is stirred at 50° C. for 12 h. After cooling, the mixture is concentrated on a rotary evaporator, the residue is taken up in dichloromethane and the solution is extracted twice with water, dried over $Na_2SO_4$ and freed from the solvent under vacuum. 3.11 g of product are obtained (94.3% purity, 83.4% yield, log P (pH 2.3)=4.50).

3-[2-(4-Chlorophenyl)ethyl]-5-[(4-methylphenyl)sulphonyl]-1,2,4-thiadiazole 10.90 g (45.1 mmol) of 5-[2-(4-chlorophenyl)ethyl]-1,3,4-oxathiazol-2-one and 8.58 g (47.4 mmol) of tosyl cyanide are stirred in 11 ml of 1,2-dichlorobenzene at 160° C. for 1 h. Subsequently, the reaction mixture is cooled and treated with 10 ml of pentane, and the precipitate is filtered off and dried under vacuum. 11.06 g of product are obtained (99.9% purity, 64.7% yield, log P (pH 2.3)=4.62).

5-[2-(4-Chlorophenyl)ethyl]-1,3,4-oxathiazol-2-one 11.60 g (88.5 mmol) of chlorocarbonylsulphenyl chloride and 13.54 g (73.8 mmol) of 3-(4-chlorophenyl)propionamide are stirred in 25 ml of toluene at 70° C. for 3 h. Subsequently, the mixture is cooled and freed from a solvent under vacuum and the residue is purified by column chromatography. 15.6 g of product are obtained (99.9% purity, 87.6% yield, log P (pH 2.3)=3.36).

Biological Examples

Example 1

*Alternaria* Test (Tomato)/Protective

Solvents: 24.5 parts by weight of acetone
24.5 parts by weight of dimethylacetamide
Emulsifier: 1 part by weight of alkylaryl polyglycol ether (polyoxyethylene (16) tristearylphenyl ether)

To prepare a suitable active substance composition, 1 part by weight of substance is mixed with the given amounts of solvents and emulsifier and the concentrate is diluted to the desired concentration using water.

For the testing of protective effectiveness, young plants are sprayed with the active substance composition in the application rate given. After the spray coating has been dried on, the plants are inoculated with an aqueous suspension of spores of *Alternaria solani*. The plants are then placed in an incubation chamber at approximately 20° C. and 100% relative humidity.

Evaluation is carried out 3 days after the inoculation. In this connection, 0% means a degree of effectiveness corresponding to that of the control, while a degree of effectiveness of 100% means that no infestation is observed.

In this test, the compounds 1, 2, 11, 12, 13, 14, 15, 17, 24, 28, 32, 33, 39, 40, 43, 44, 47 and 48 according to the invention show, at a concentration of active substance of 100 ppm, a degree of effectiveness of 70% or more.

Example 2

*Uromyces* Test (Beans)/Protective

Solvents: 24.5 parts by weight of acetone
24.5 parts by weight of dimethylacetamide
Emulsifier: 1 part by weight of alkylaryl polyglycol ether (polyoxyethylene (16) tristearylphenyl ether)

To prepare a suitable active substance composition, 1 part by weight of active substance is mixed with the given amounts of solvents and emulsifier and the concentrate is diluted to the desired concentration using water.

For the testing of protective effectiveness, young plants are sprayed with the active substance composition in the application rate given. After the spray coating has been dried on, the plants are inoculated with an aqueous suspension of the spores of the bean rust pathogen *Uromyces appendiculatus* and then remain in an incubation chamber at approximately 20° C. and 100% relative humidity for 1 day.

The plants are then placed in a greenhouse at approximately 21° C. and a relative humidity of approximately 90%.

Evaluation is carried out 10 days after the inoculation. In this connection, 0% means a degree of effectiveness corresponding to that of the control, while a degree of effectiveness of 100% means that no infestation is observed.

In this test, the compounds 1, 2, 6, 8, 14, 15, 18, 17, 32, 38, 39, 43, 44 and 47 according to the invention show, at a concentration of active substance of 100 ppm, a degree of effectiveness of 70% or more.

Example 3

*Sphaerotheca* Test (Cucumber)/Protective

Solvent: 49 parts by weight of N,N-dimethylformamide
Emulsifier: 1 part by weight of alkylaryl polyglycol ether (polyoxyethylene (16) tristearylphenyl ether)

To prepare a suitable active substance composition, 1 part by weight of active substance is mixed with the given amounts of solvents and emulsifier and the concentrate is diluted to the desired concentration using water.

For the testing of protective effectiveness, young cucumber plants are sprayed with the active substance composition in the application rate given. One day after treatment, the plants are inoculated with a suspension of spores of *Sphaerotheca fuliginea*. The plants are then placed in a greenhouse at 70% relative humidity and a temperature of 23° C.

Evaluation is carried out 7 days after the inoculation. In this connection, 0% means a degree of effectiveness corresponding to that of the control, while a degree of effectiveness of 100% means that no infestation is observed.

In this test, the compounds 1, 2, 3, 4, 5, 6, 7, 8, 9, 11, 12, 13, 14, 15, 16, 17, 18, 20, 21, 22, 23, 24, 25, 26, 28, 29, 30, 31, 32, 33, 34, 35, 36, 37, 38, 39, 40, 41, 42, 43, 44, 45, 47 and 48 according to the invention show, at a concentration of active substance of 500 ppm, a degree of effectiveness of 70% or more.

Example 4

*Puccinia Triticina* Test (Wheat)/Protective

Solvent: 50 parts by weight of N,N-dimethylacetamide
Emulsifier: 1 part by weight of alkylaryl polyglycol ether (polyoxyethylene (16) tristearylphenyl ether)

To prepare a suitable active substance composition, 1 part by weight of active substance is mixed with the given amounts of solvent and emulsifier and the concentrate is diluted to the desired concentration using water.

For the testing of protective effectiveness, young plants are sprayed with the active substance composition in the application rate given. After the spray coating has been dried on, the plants are sprayed with a suspension of spores of *Puccinia triticina*. The plants remain in an incubation chamber at 20° C. and 100% relative humidity for 48 hours. The plants are placed in a greenhouse at a temperature of approximately 20° C. and a relative humidity of approximately 80%.

Evaluation is carried out 8 days after the inoculation. In this connection, 0% means a degree of effectiveness corresponding to that of the control, while a degree of effectiveness of 100% means that no infestation is observed.

In this test, the compounds 1, 2, 3, 4, 5, 6, 9, 11, 13, 14, 15, 17, 18, 20, 24, 25, 26, 28, 29, 31, 32, 33, 34, 35, 38, 39, 40, 47 and 48 according to the invention show, at a concentration of active substance of 500 ppm, a degree of effectiveness of 70% or more.

Example 5

*Puccinia Triticina* Test (Wheat)/Curative

Solvent: 50 parts by weight of N,N-dimethylacetamide
Emulsifier: 1 part by weight of alkylaryl polyglycol ether (polyoxyethylene (16) tristearylphenyl ether)

To prepare a suitable active substance composition, 1 part by weight of active substance is mixed with the given amounts of solvent and emulsifier and the concentrate is diluted to the desired concentration using water.

For the testing of curative effectiveness, young plants are sprayed with a suspension of spores of *Puccinia triticina*. The plants remain in an incubation chamber at 20° C. and 100% relative humidity for 48 hours and are then sprayed with the active substance composition in the application rate given. The plants are placed in a greenhouse at a temperature of approximately 20° C. and a relative humidity of approximately 80%.

Evaluation is carried out 8 days after the inoculation. In this connection, 0% means a degree of effectiveness corresponding to that of the control, while a degree of effectiveness of 100% means that no infestation is observed.

In this test, the compounds 1, 2, 3, 4, 5, 6, 9, 11, 13, 14, 15, 17, 18, 19, 20, 24, 25, 26, 29, 31, 32, 33, 34, 35, 36, 38, 39, 40, 47 and 48 according to the invention show, at a concentration of active substance of 500 ppm, a degree of effectiveness of 70% or more.

Example 6

*Phakopsora* Test (Soya)/Protective

Solvent: 28.5 parts by weight of acetone
Emulsifier: 1.5 parts by weight of polyoxyethylene alkylphenyl ether (polyoxyethylene (16) tristearylphenyl ether)

To prepare a suitable active substance composition, 1 part by weight of active substance is mixed with given amounts of solvent and emulsifier and the concentrate is diluted to the desired concentration using water.

For the testing of protective effectiveness, young plants are sprayed with the active substance composition in the application rate given. One day after spraying, the plants are sprayed with an aqueous suspension of spores of *Phakopsora pachyrhizi*. The plants remain in a greenhouse at 20° C. and 80% relative humidity.

Evaluation is carried out 11 days after the inoculation. In this connection, 0% means a degree of effectiveness corresponding to that of the control, while a degree of effectiveness of 100% means that no infestation is observed.

In this test, the compounds 1, 2, 14, 32 and 47 according to the invention show, at a concentration of active substance of 100 ppm, a degree of effectiveness of 80% or more.

Example 7

*Phaedon* Test (PHAECO Spray Treatment)

Solvents: 78.0 parts by weight of acetone
 1.5 parts by weight of dimethylformamide
Emulsifier: 0.5 part by weight of alkylaryl polyglycol ether To prepare a suitable active substance composition, 1 part by weight of active substance is mixed with the given amounts of solvents and emulsifier and the concentrate is diluted to the desired concentration using water which contains emulsifier.

Discs of Chinese cabbage leaves (*Brassica pekinensis*) are sprayed with an active substance composition of the desired concentration and, after drying, stocked with larvae of the mustard beetle (*Phaedon cochleariae*).

After 7 days, the effectiveness is determined in %. In this connection, 100% means that all beetle larvae have been killed; 0% means that no beetle larvae have been killed.

In this test, e.g., the following compounds of the preparation examples show an effectiveness of ≧80% at an application rate of 500 g/ha:
 Ex. No.: 3 and 8.

The invention claimed is:

1. A thiadiazolyloxyphenylamidine of formula (I)

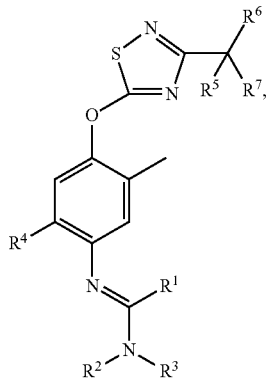

in which

R¹ is chosen from hydrogen; linear or branched $C_{1-12}$-alkyl, $C_{2-12}$-alkenyl or $C_{2-12}$-alkynyl or cyclic $C_{3-8}$-alkyl, $C_{4-8}$-alkenyl or $C_{4-8}$-alkynyl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR'$_2$, R' being hydrogen or a $C_{1-12}$-alkyl group, and X being a halogen atom; —SH; —SR", R" being a $C_{1-12}$-alkyl group which can be substituted with one or more groups chosen from —R', —X, —OR', —SR', —NR'$_2$, —SiR'$_3$, —COOR', —CN and —CONR$_2$', R' having the above meanings;

R² is chosen from linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

R³ is chosen from —CN, —SH, —SR", —OR", —(C=O)—R", R" having the above meanings; linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

or in which

R² and R³,
R² and R¹ or
R¹ and R³ can form, together with the atoms to which they are bonded or with additional atoms chosen from nitrogen, oxygen, phosphorus and sulphur, a four- to seven-membered ring which can be substituted with R', OR', SR', NR'$_2$ or SiR'$_3$ groups, R' having the above meanings;

R⁴ is chosen from the group consisting of —X and —CN;

R⁵, R⁶ and R⁷ are chosen, independently of one another, from hydrogen, linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl groups or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, alkoxy (—OR'), thioether or mercapto (—SR'), amino (—NR'$_2$), silyl (—SiR'$_3$), carboxyl (—COOR'), cyano (—CN) and amide (—CONR$_2$') groups, R' having the above meanings;

or

R⁵ and R⁶, R⁶ and R⁷ or R⁵ and R⁷ can form, together with the carbon atom to which they are bonded or with additional atoms chosen from nitrogen, oxygen, phosphorus and sulphur, a three- to seven-membered ring which can be substituted with X, R', OR', SR', NR'$_2$, SiR'$_3$, $C_{15-18}$-aryl, $C_{7-19}$-aralkyl or $C_{7-19}$-alkaryl groups, R' having the above meanings and it being possible for the aryl, aralkyl or alkaryl groups to be substituted in the ring with X, R', OR' or SR' groups;

or

R⁵ and R⁶, R⁶ and R⁷ or R⁵ and R⁷ can form, together with the carbon atom to which they are bonded, a double bond which can be substituted with —CN, —SH, —SR", —OR", or —(C=O)—R", R" having the above meanings; or linear or branched $C_{1-12}$-alkyl, $C_{2-12}$-alkenyl or $C_{2-12}$-alkynyl, cyclic $C_{3-8}$-alkyl, $C_{4-8}$-alkenyl or $C_{4-8}$-alkynyl or $C_{5-18}$-aryl, $C_{7-19}$-aralkyl or $C_{7-19}$-alkaryl groups, it being possible, in the ring system of all abovementioned cyclic groups, for one or more carbon atoms to be replaced by heteroatoms chosen from nitrogen, oxygen, phosphorus and sulphur and it being possible for all abovementioned groups to be substituted with one or more groups chosen from —R', —X, —OR', —SR', —NR'$_2$, —SiR'$_3$, —COOR', —CN and —CONR$_2$', R' having the above meanings;

or a salt thereof.

2. A thiadiazolyloxyphenylamidine of formula (I) according to claim 1, in which

R¹ is chosen from the group consisting of hydrogen, a mercapto group (—SH) or $C_{1-8}$-alkyl groups;

R² is chosen from linear or branched $C_{1-8}$-alkyl groups;

R³ is chosen from linear, branched and alicyclic $C_{1-8}$-alkyl groups;

or in which

R² and R³ can form, together with the nitrogen atom to which they are bonded or with additional atoms chosen from nitrogen and oxygen, a five- to six-membered ring which can be substituted with one or more $C_{1-12}$-alkyl groups;

R⁴ is chosen from the group consisting of F, Cl, Br and I;

R⁵ and R⁶ are chosen, independently of one another, from hydrogen and linear $C_{1-8}$-alkyl groups;

R⁷ is chosen from the group consisting of hydrogen, linear, branched, alicyclic or heterocyclic $C_{1-12}$-alkyl groups, halogen atoms, $C_{1-4}$-haloalkyl groups, phenyl groups and benzyl groups, it being possible for the phenyl or benzyl groups to be substituted with one or more atoms chosen from —R', —X, —OR', —SR', —NR'$_2$, —SiR'$_3$, —COOR', —CN and —CONR$_2$';
or R$^5$ and R$^6$ can form, together with the carbon atom to which they are bonded or with additional atoms chosen from nitrogen, oxygen, phosphorus and sulphur, a three-, four- or five-membered ring which can be substituted with X, R' or phenyl groups, R' having the above meanings, and R$^7$ is chosen from hydrogen, halogen atoms, phenyl groups, phenoxy groups and benzyl groups, it being possible for the abovementioned groups to be substituted by one, two or more halogen atoms;
or R$^5$ and R$^6$ can form, together with the carbon atom to which they are bonded, a double bond which can be substituted with hydrogen, linear or branched C$_{1-12}$-alkyl groups or cyclic C$_{3-8}$-alkyl groups, halogen atoms, C$_{1-4}$-haloalkyl groups, phenyl groups and benzyl groups, it being possible for the abovementioned phenyl or benzyl groups to be substituted with one or more atoms chosen from —R', —X, —OR', —SR', —NR'$_2$, —SiR'$_3$, —COOR', —CN and —CONR$_2$'

R$^7$ is hydrogen or C$_{1-4}$-alkyl;
or a salt thereof.

3. A thiadiazolyloxyphenylamidine of formula (I) according to claim 1, in which R$^1$ is chosen from the group consisting of hydrogen, mercapto and methyl;

R$^2$ is chosen from the group consisting of methyl and ethyl;

R$^3$ is chosen from the group consisting of methyl, ethyl and isopropyl;
or in which R$^2$ and R$^3$ form, together with the nitrogen atom to which they are bonded, a piperidyl, pyrrolidyl or 2,6-dimethylmorpholinyl radical;

R$^4$ is chosen from the group consisting of Cl and Br;

R$^5$ and R$^6$ are chosen, independently of one another, from hydrogen, methyl groups and ethyl groups or can form, together with the carbon atom to which they are bonded, a cyclopropyl ring which can be substituted with one or two chlorine or bromine atoms or with a phenyl or halophenyl group, and R$^7$ is chosen from the group consisting of methyl, methoxy, ethoxy, trimethylsilyl, triethylsilyl, phenyl, benzyl, 4-chlorobenzyl, 4-chlorophenyl, 4-bromophenyl, 2,4-dichlorophenyl, 2-chlorophenoxy, 3-chlorophenoxy, 4-chlorophenoxy and 3-trifluoromethyl groups;
or R$^5$ and R$^6$ can form, together with the carbon atom to which they are bonded, a double bond which is substituted with a 4-fluorophenyl group, and R$^7$ is hydrogen or C$_{1-4}$-alkyl;
or a salt thereof.

4. A thiadiazolyloxyphenylamidine of formula (I) or salt according to claim 1, in which R$^7$ is a phenyl or benzyl group which in each case is substituted in the 4-position with chlorine or bromine.

5. Thiadiazolyloxyphenylamidine or salt selected from the group consisting of N'-{4-[(3-(tert-butyl)-1,2,4-thiadiazol-5-yl)oxy]-2-chloro-5-methylphenyl}-N-ethyl-N-methylimidoformamide; N'-{2-bromo-4-[(3-(tert-butyl)-1,2,4-thiadiazol-5-yl)oxy]-5-methylphenyl}-N-ethyl-N-methylimidoformamide; N'-(2-chloro-4-{[3-(1-chlorocyclopropyl)-1,2,4-thiadiazol-5-yl]oxy}-5-methylphenyl)-N-ethyl-N-methylimidoformamide; N'-(2-chloro-4-{[3-(1-chlorocyclopropyl)-1,2,4-thiadiazol-5-yl]oxy}-5-methylphenyl)-N-methyl-N-(propan-2-yl)imidoformamide; 2-chloro-4-{[3-(1-chlorocyclopropyl)-1,2,4-thiadiazol-5-yl]oxy}-5-methyl-N-[(E)-piperidin-1-ylmethylidene]aniline; N'-[2-chloro-4-({3-[1-(4-chlorophenyl)ethyl]-1,2,4-thiadiazol-5-yl}oxy)-5-methylphenyl]-N-ethyl-N-methylimidoformamide; 2-chloro-4-({3-[1-(4-chlorophenyl)ethyl]-1,2,4-thiadiazol-5-yl}oxy)-5-methyl-N-[(E)-piperidin-1-ylmethylidene]aniline; N'-[2-chloro-4-({3-[1-(4-chlorophenyl)ethyl]-1,2,4-thiadiazol-5-yl}oxy)-5-methylphenyl]-N-methyl-N-(propan-2-yl)imidoformamide; N'-[2-chloro-4-({3-[2-(4-chlorophenyl)ethyl]-1,2,4-thiadiazol-5-yl}oxy)-5-methylphenyl]-N-ethyl-N-methylimidoformamide; 2-chloro-4-({3-[2-(4-chlorophenyl)ethyl]-1,2,4-thiadiazol-5-yl}oxy)-5-methyl-N-[(Z)-piperidin-1-ylmethylidene]aniline; N'-[2-chloro-4-({3-[2-(4-chlorophenyl)propan-2-yl]-1,2,4-thiadiazol-5-yl}oxy)-5-methylphenyl]-N-ethyl-N-methylimidoformamide; 2-chloro-4-({3-[2-(4-chlorophenyl)propan-2-yl]-1,2,4-thiadiazol-5-yl}oxy)-5-methyl-N-[(Z)-piperidin-1-ylmethylidene]aniline; N'-[2-chloro-4-({3-[2-(4-chlorophenyl)propan-2-yl]-1,2,4-thiadiazol-5-yl}oxy)-5-methylphenyl]-N-methyl-N-(propan-2-yl)imidoformamide; N'-{4-[(3-benzyl-1,2,4-thiadiazol-5-yl)oxy]-2-chloro-5-methylphenyl}-N-ethyl-N-methylimidoformamide; N'-[2-chloro-4-({3-[(E)-2-(4-fluorophenyl)ethenyl]-1,2,4-thiadiazol-5-yl}oxy)-5-methylphenyl]-N-ethyl-N-methylimidoformamide; 2-chloro-4-({3-[(E)-2-(4-fluorophenyl)ethenyl]-1,2,4-thiadiazol-5-yl}oxy)-5-methyl-N-[(Z)-piperidin-1-ylmethylidene]aniline; N'-[2-chloro-4-({3-[1-(4-chlorophenyl)cyclopropyl]-1,2,4-thiadiazol-5-yl}oxy)-5-methylphenyl]-N-ethyl-N-methylimidoformamide; N'-(2-chloro-4-{[3-(4-chlorobenzyl)-1,2,4-thiadiazol-5-yl]oxy}-5-methylphenyl)-N-ethyl-N-methylimidoformamide (Example 18); N'-(2-chloro-4-{[3-(chloromethyl)-1,2,4-thiadiazol-5-yl]oxy}-5-methylphenyl)-N-ethyl-N-methylimidoformamide; N'-[2-chloro-4-({3-[1-(4-chlorophenyl)cyclopropyl]-1,2,4-thiadiazol-5-yl}oxy)-5-methylphenyl]-N-methyl-N-(propan-2-yl)imidoformamide; 2-chloro-4-({3-[1-(4-chlorophenyl)cyclopropyl]-1,2,4-thiadiazol-5-yl}oxy)-5-methyl-N-[(Z)-piperidin-1-ylmethylidene]aniline; N'-[2-chloro-4-({3-[(4-chlorophenoxy)methyl]-1,2,4-thiadiazol-5-yl}oxy)-5-methylphenyl]-N-ethyl-N-methylimidoformamide; N'-[2-chloro-4-({3-[(E)-2-(4-fluorophenyl)ethenyl]-1,2,4-thiadiazol-5-yl}oxy)-5-methylphenyl]-N-methyl-N-(propan-2-yl)imidoformamide; N'-{4-[(3-(tert-butyl)-1,2,4-thiadiazol-5-yl)oxy]-2-chloro-5-methylphenyl}-N-methyl-N-propylimidoformamide (Example 24); N'-{4-[(3-(tert-butyl)-1,2,4-thiadiazol-5-yl)oxy]-2-chloro-5-methylphenyl}-N-methyl-N-(prop-2-en-1-yl)imidoformamide; N'-{4-[(3-(tert-butyl)-1,2,4-thiadiazol-5-yl)oxy]-2-chloro-5-methylphenyl}-N-(cyclopropylmethyl)-N-methylimidoformamide; N'-{4-[(3-(tert-butyl)-1,2,4-thiadiazol-5-yl)oxy]-2-chloro-5-methylphenyl}-N-(3-methoxypropyl)-N-methylimidoformamide; N'-(2-chloro-5-methyl-4-{[3-(2-methyl-1-phenylpropan-2-yl)-1,2,4-thiadiazol-5-yl]oxy}phenyl)-N-ethyl-N-methylimidoformamide); rel-N'-[2-chloro-5-methyl-4-({3-[(1R,2R)-2-phenylcyclopropyl]-1,2,4-thiadiazol-5-yl}oxy)phenyl]-N-ethyl-N-methylimidoformamide; rel-2-chloro-5-methyl-4-({3-[(1R,2R)-2-phenylcyclopropyl]-1,2,4-thiadiazol-5-yl}oxy)-N-[(E)-piperidin-1-ylmethylidene]aniline; rel-N'-[2-chloro-5-methyl-4-({3-[(1R,2R)-2-phenylcyclopropyl]-1,2,4-thiadiazol-5-yl}oxy)phenyl]-N-methyl-N-(propan-2-yl)imidoformamide; N'-(2-chloro-4-{[3-(2,2-dichloro-1-methylcyclopropyl)-1,2,4-thiadiazol-5-yl]oxy}-5-methylphenyl)-N-ethyl-N-methylimidoformamide; N'-(4-{[3-(4-bromobenzyl)-1,2,4- thiadiazol-5-yl]oxy}-2-chloro-5-methylphenyl)-N-ethyl-N-methylimidoformamide (Example 33); N'-[2-chloro-5-methyl-4-({3-[3-(trifluoromethyl)benzyl]-1,2,4-thiadiazol-5-yl}oxy)phenyl]-N-ethyl-N-methylimidoformamide; N'-[2-chloro-4-({3-[(3-chlorophenoxy)methyl]-1,2,4-thiadiazol-5-yl}oxy)-5-methylphenyl]-N-ethyl-N-methylimidoformamide; N'-[2-chloro-4-({3-[(2-chlorophenoxy)methyl]-1,2,4-thiadiazol-5-yl}oxy)-5-methylphenyl]-N-ethyl-N-methylimidoformamide; N'-(2-chloro-5-methyl-4-{[3-(phenoxymethyl)-1,2,4-thiadiazol-5-yl]oxy}phenyl)-N-ethyl-N-methylimidoformamide; N'-(2-chloro-4-{[3-(2,4-dichlorobenzyl)-1,2,4-thiadiazol-5-yl]oxy}-5-methylphenyl)-N-ethyl-N-methylimidoformamide; N'-(2-chloro-4-{[3-(1-chloro-2-methylpropan-2-yl)-1,2,4-thiadiazol-5-yl]oxy}-5-methylphenyl)-N-ethyl-N-methylimidoformamide; and N'-(2-chloro-4-{[3-(2,4-difluorobenzyl)-1,2,4-thiadiazol-5-yl]oxy}-5-methylphenyl)-N-ethyl-N-methylimidoformamide.

6. Process for the preparation of the thiadiazolyloxyphenylamidine or salt according to claim 1 comprising at least one of the following stages (a) to (j):

(a) reaction of nitrobenzene derivatives of the formula (III) with a thiadiazolyl alcohol of the formula (II) according to the following reaction scheme:

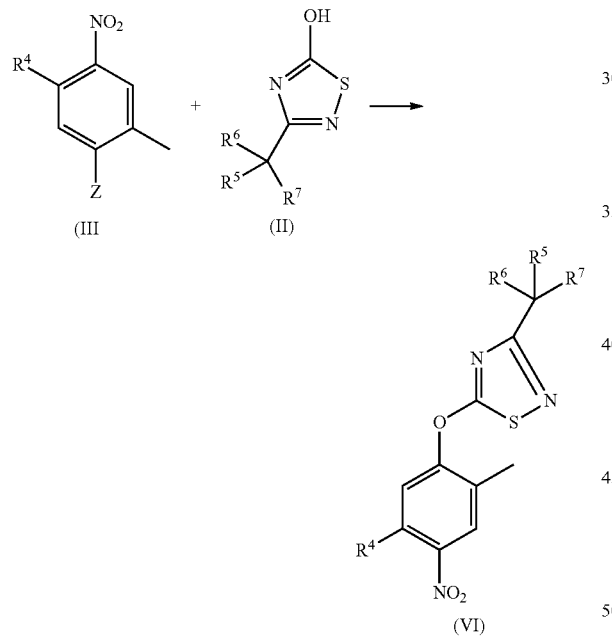

(b) reaction of nitrophenol derivatives of the formula (V) with thiadiazolyl derivatives of the formula (IV) according to the following reaction scheme:

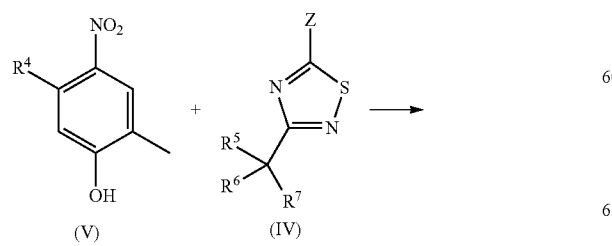

(c) reaction of anilines of the formula (VII) with a thiadiazolyl alcohol of the formula (II) according to the following reaction scheme:

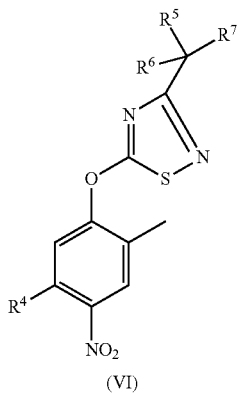

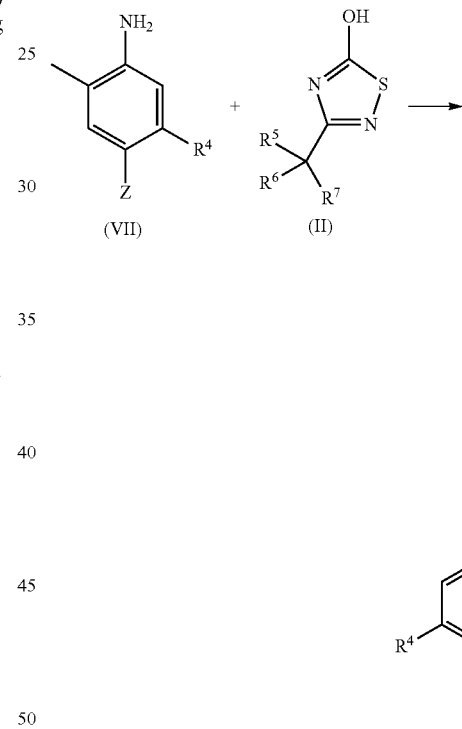

(d) reaction of aminophenols of the formula (XII) with thiadiazolyl derivatives of the formula (IV) according to the following reaction scheme:

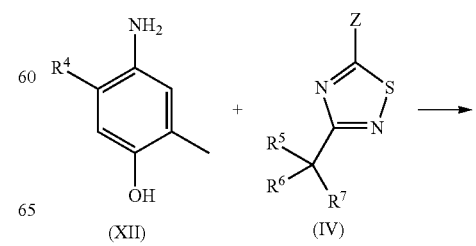

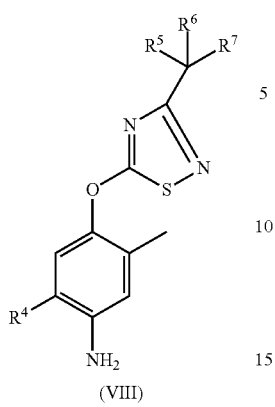

(VIII)

(e) reduction of the nitrophenoxy ethers of the formula (VI) to give aniline ethers of the formula (VIII) according to the following reaction scheme:

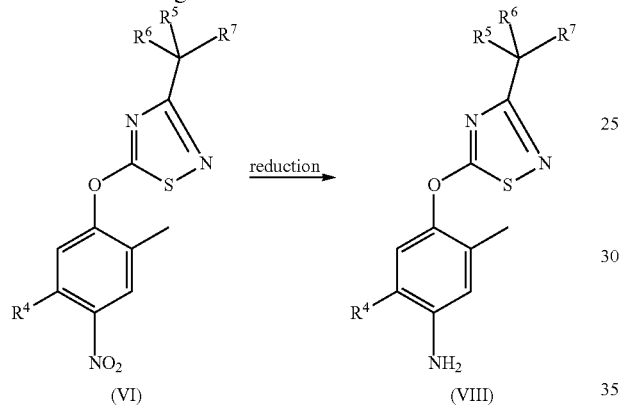

(f) reaction of the aniline ethers of the formula (VIII) with
(i) aminoacetals of the formula (XIII) or
(ii) amides of the formula (XIV) or
(iii) amines of the formula (XV) in the presence of orthoesters of the formula (XVI) according to the following reaction scheme:

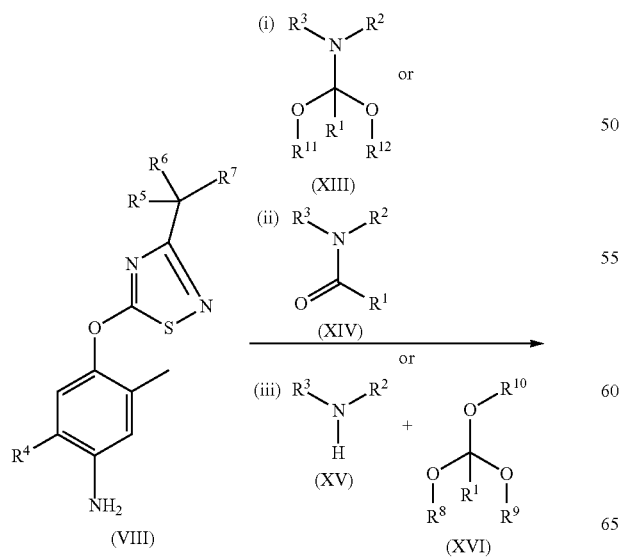

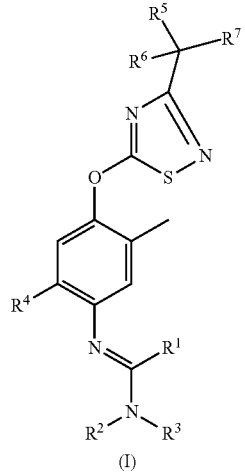

(I)

(g) reaction of the aminophenols of the formula (XII) with
(i) aminoacetals of the formula (XIII) or
(ii) amides of the formula (XIV) or
(iii) amines of the formula (XV) in the presence of orthoesters of the formula (XVI) according to the following reaction scheme:

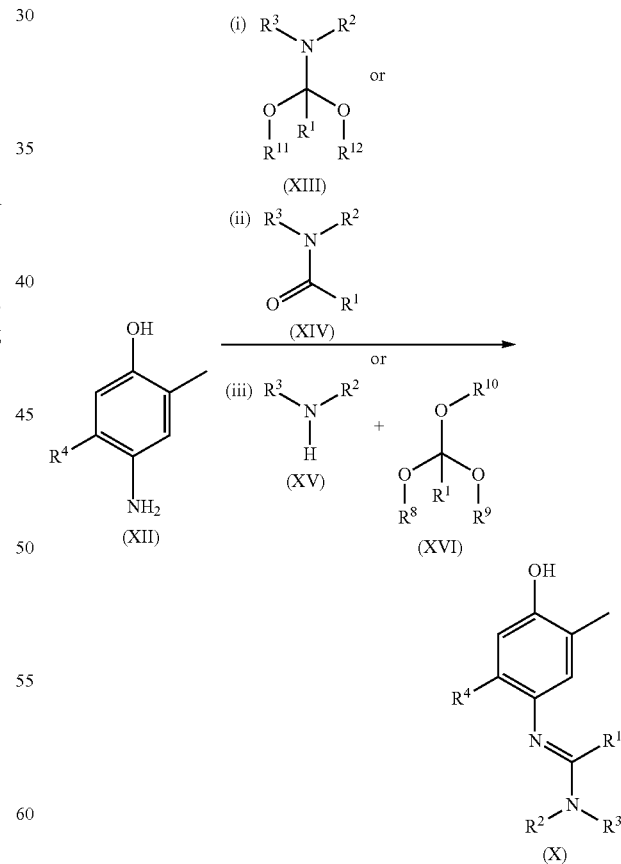

(h) reaction of the aminophenols of the formula (VII) with
(i) aminoacetals of the formula (XIII) or
(ii) amides of the formula (XIV) or (iii) amines of the formula (XV) in the presence of orthoesters of the formula (XVI) according to the following reaction scheme:

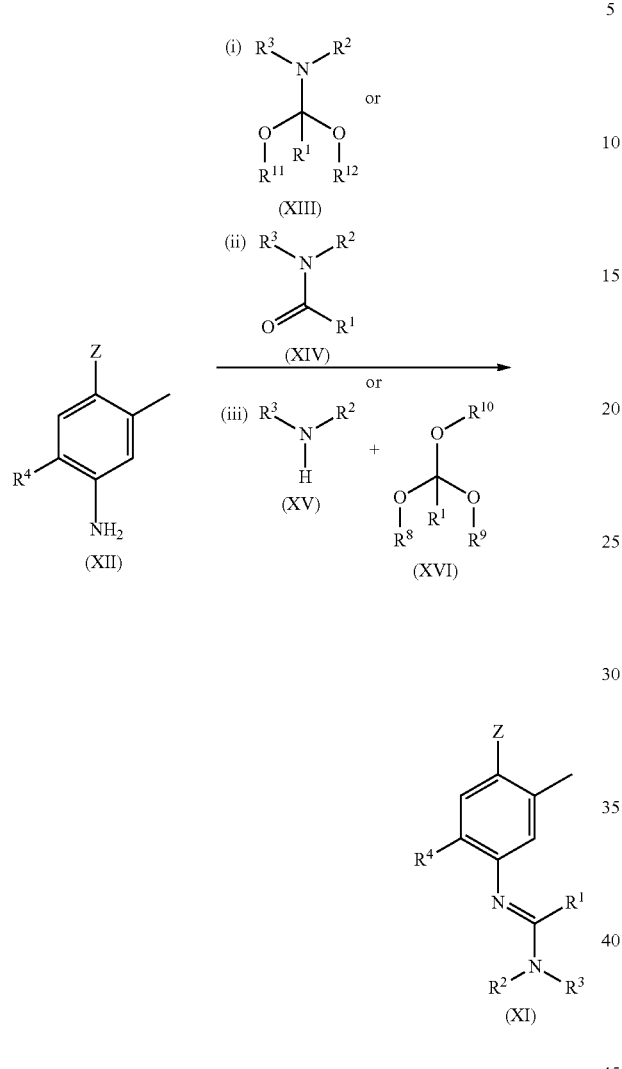

(i) reaction of amidines of the formula (XI) with a thiadiazolyl alcohol of the formula (II) according to the following reaction scheme:

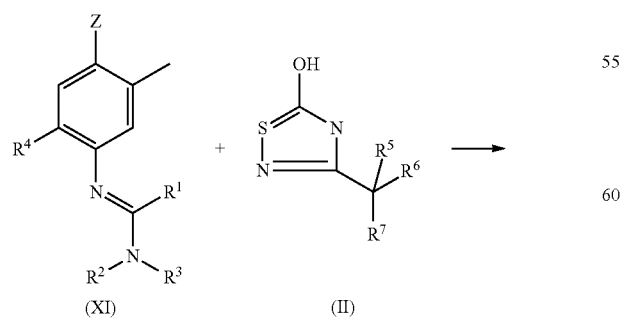

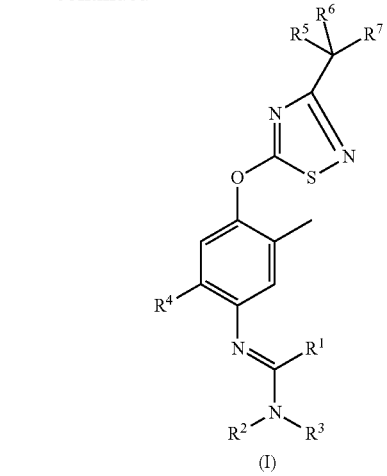

(j) reaction of amidines of the formula (XI) with thiadiazolyl derivatives of the formula (IV) according to the following reaction scheme:

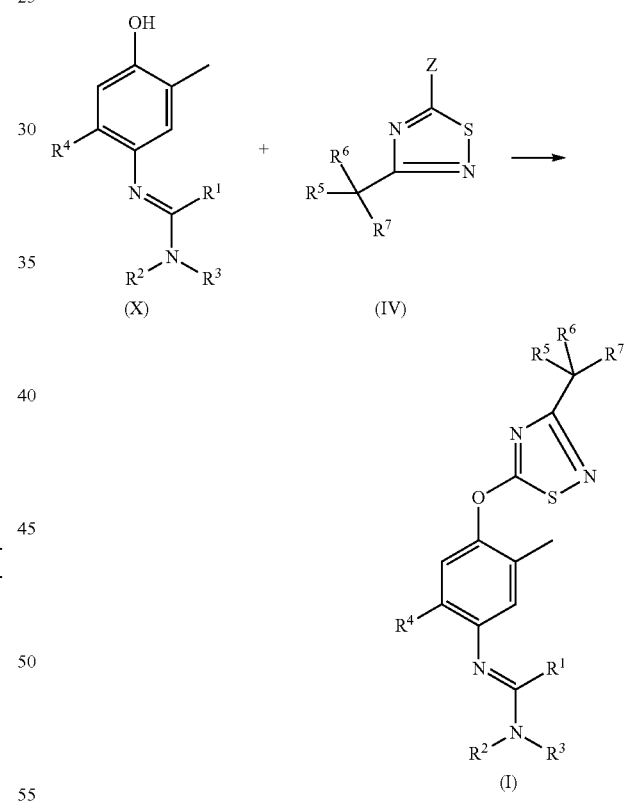

in which, in the above schemes,

Z is a leaving group;

and $R^8$ to $R^{10}$ are chosen, independently of one another, from the group consisting of hydrogen, $C_{1-12}$-alkyl, $C_{2-12}$-alkenyl, $C_{2-12}$-alkynyl, $C_{5-18}$-aryl, $C_{7-19}$-arylalkyl and $C_{7-19}$-alkylaryl groups and in each case $R^8$ with $R^9$, $R^8$ with $R^{10}$ or $R^9$ with $R^{10}$ can form, together with the atoms to which they are bonded and if appropriate with additional carbon, nitrogen, oxygen or sulphur atoms, a five-, six- or seven-membered ring;

$R^{11}$ and $R^{12}$ are chosen, independently of one another, from the group consisting of hydrogen, $C_{1-12}$-alkyl, $C_{2-12}$-alkenyl, $C_{2-12}$-alkynyl, $C_{5-18}$-aryl and $C_{7-19}$-arylalkyl groups and can form, together with the atoms to which they are bonded, a five-, six- or seven-membered ring.

7. Composition for combating undesirable microorganisms, comprising at least one thiadiazolyloxyphenylamidine or salt according to claim 1.

8. A thiadiazolyloxyphenylamidine or salt according to claim 1 that is adapted for combating undesirable microorganisms.

9. Method for combating undesirable microorganisms, comprising applying at least one thiadiazolyloxyphenylamidine or salt according to claim 1 to the microorganisms and/or to a habitat thereof.

10. Seed, which is treated with at least one thiadiazolyloxyphenylamidine or salt according to claim 1.

11. A thiadiazolyloxyphenylamidine or salt according to claim 1 in which
   $R^1$ is hydrogen;
   $R^2$ is ethyl; and
   $R^3$ is methyl.

12. A thiadiazolyloxyphenylamidine or salt according to claim 1 in which
   $R^5$ is methyl;
   $R^6$ is methyl; and
   $R^7$ is methyl.

13. A thiadiazolyloxyphenylamidine or salt according to claim 1 in which
   $R^1$ is hydrogen;
   $R^2$ is ethyl;
   $R^3$ is methyl;
   $R^4$ is Cl;
   $R^5$ is methyl;
   $R^6$ is methyl; and
   $R^7$ is methyl.

14. A composition according to claim 7, wherein the composition comprises between 0.5% and 90% by weight of at least one thiadiazolyloxyphenylamidine or salt.

* * * * *